(12) United States Patent
Verma et al.

(10) Patent No.: US 11,660,054 B2
(45) Date of Patent: May 30, 2023

(54) MEDICAL DIAGNOSTIC AND TREATMENT SYSTEMS AND THEIR METHODS OF USE

(71) Applicant: Biogen MA Inc., Cambridge, MA (US)

(72) Inventors: Ajay Verma, Needham, MA (US); Elliot Greenblatt, Cambridge, MA (US); Ira Spool, Chestnut Hill, MA (US); Seth O. Newburg, Arlington, MA (US); Guy M. Danner, Somerville, MA (US); Ara N. Knaian, Newton, MA (US); Rachel M. Chaney, Nahant, MA (US); John W. Hoppin, Boston, MA (US)

(73) Assignee: Biogen MA Inc., Cambridge, MA (US)

( * ) Notice: Subject to any disclaimer, the term of this patent is extended or adjusted under 35 U.S.C. 154(b) by 802 days.

(21) Appl. No.: 16/462,518

(22) PCT Filed: Nov. 22, 2017

(86) PCT No.: PCT/US2017/062937
§ 371 (c)(1),
(2) Date: May 20, 2019

(87) PCT Pub. No.: WO2018/098221
PCT Pub. Date: May 31, 2018

(65) Prior Publication Data
US 2019/0320989 A1  Oct. 24, 2019

Related U.S. Application Data

(60) Provisional application No. 62/425,361, filed on Nov. 22, 2016.

(51) Int. Cl.
*A61B 6/03* (2006.01)
*G01T 1/16* (2006.01)
(Continued)

(52) U.S. Cl.
CPC ............ *A61B 6/037* (2013.01); *A61B 5/6803* (2013.01); *A61B 5/6805* (2013.01);
(Continued)

(58) Field of Classification Search
CPC ..... A61B 6/037; A61B 6/4258; A61B 6/4266; A61B 6/4275; A61B 6/501; A61B 6/4405;
(Continued)

(56) References Cited

U.S. PATENT DOCUMENTS

| 4,682,604 A | 7/1987 | Fymat et al. |
| 5,007,427 A | 4/1991 | Suzuki et al. |

(Continued)

FOREIGN PATENT DOCUMENTS

WO    WO 2010/033159 A1    3/2010

OTHER PUBLICATIONS

Yamamoto, Seiichi, et al. "Development of a brain PET system, PET-Hat: awearable PET system forbrain research." IEEE Transactions on Nuclear Science 58.3 (2011): 668-673. (Year: 2011).*

(Continued)

*Primary Examiner* — Sean D Mattson
(74) *Attorney, Agent, or Firm* — Wolf, Greenfield & Sacks, P.C.

(57) ABSTRACT

Embodiments related to methods and wearable medical detecting systems for detecting disease states and/or treatment states of a subject are described. In one embodiment, a wearable structure may include one or more radiation detectors use to detect a time varying radiation signal emitted from a labeled compound within a body portion of interest. The radiation signal may be analyzed to determine one or more signal characteristics that may be compared to one or more predetermined standard characteristics associ- (Continued)

ated with known disease and/or treatment states to determine a current disease and/or treatment state of a subject.

20 Claims, 15 Drawing Sheets

(51) Int. Cl.
  *A61B 5/00* (2006.01)
  *A61B 6/00* (2006.01)
(52) U.S. Cl.
  CPC .......... *A61B 6/4258* (2013.01); *A61B 6/4266* (2013.01); *G01T 1/16* (2013.01)
(58) Field of Classification Search
  CPC ..... A61B 6/4429; A61B 6/506; A61B 5/6803; A61B 5/6805; A61B 5/02755; A61B 5/0022; A61B 2562/043; G01T 1/16; A61F 2007/0064; A61F 2007/0075; A61F 2007/0093; A61F 2007/0096; A61F 2007/0233; A61F 7/10
  See application file for complete search history.

(56) References Cited

U.S. PATENT DOCUMENTS

| | | | |
|---|---|---|---|
| 5,647,363 A | 7/1997 | Rabito et al. | |
| 5,800,351 A * | 9/1998 | Mann | A61B 5/291 607/139 |
| 6,242,743 B1 | 6/2001 | DeVito et al. | |
| 6,429,431 B1 * | 8/2002 | Wilk | G01T 7/00 250/363.01 |
| 6,574,513 B1 | 6/2003 | Collura et al. | |
| 6,583,420 B1 | 6/2003 | Nelson et al. | |
| 7,015,460 B2 | 3/2006 | Nelson et al. | |
| 7,500,746 B1 | 3/2009 | Howell et al. | |
| 7,541,599 B2 | 6/2009 | Moritake et al. | |
| 7,884,331 B2 * | 2/2011 | Majewski | A61B 6/037 250/363.04 |
| 9,226,717 B2 | 1/2016 | Tashima et al. | |
| 9,606,245 B1 * | 3/2017 | Czarnecki | A61B 6/501 |
| D795,890 S | 8/2017 | Veima et al. | |
| 9,924,913 B2 | 3/2018 | Majewski et al. | |
| 10,206,639 B2 | 2/2019 | Veima et al. | |
| 2009/0299210 A1 | 12/2009 | Marcarian | |
| 2011/0054577 A1 | 3/2011 | Latham | |
| 2014/0012108 A1 | 1/2014 | McPeak | |
| 2015/0115162 A1 * | 4/2015 | Tashima | A61B 6/037 250/363.03 |
| 2015/0119704 A1 * | 4/2015 | Roth | A61B 6/4258 600/425 |
| 2015/0182121 A1 | 7/2015 | Barbour et al. | |
| 2015/0346353 A1 | 12/2015 | Gray | |
| 2016/0008204 A1 | 1/2016 | Elliot | |
| 2016/0029983 A1 | 2/2016 | Veima et al. | |
| 2016/0058644 A1 | 3/2016 | Cheathan, III et al. | |
| 2016/0166219 A1 * | 6/2016 | Majewski | A61B 6/501 250/362 |
| 2017/0086763 A1 | 3/2017 | Veima et al. | |
| 2019/0320989 A1 | 10/2019 | Verma et al. | |

OTHER PUBLICATIONS

International Search Report and Written Opinion for International Application No. PCT/US2017/062937, dated Mar. 26, 2018.
[No Author Listed] Portable PET Helmet Captures Images of the Human Brain in Motion. Mary Babb Randolph Cancer Center. http://www.pethelmet.org/single-post/2015/06/10/Portable-PET-helmet-captures-images-of-the-human-brain-in-motion [dated Jun. 9, 2015; last accessed Jan. 12, 2017].
Ishaque, Imaging the Brain in Real-Time with a PET-Enabled "Helmet-Cam". http//www.globalresearch.com/blog/imaging-brain-real-time-pet-enabled-helmet-cam [dated. Sep. 30, 2014; last accessed Dec. 15, 2016] 5 pages.
Lewis, Wearable Brain Scanner Measures Activity on the Go. http//www.pethelmet.org/single-post/2015/01/23/Wearable-Brain-Scanner-Measures-Activity-on-the-Go [dated Jan. 23, 2015; Last accessed Jan. 12, 2017].
Bauer et al., Concept of an upright wearable positron emission tomography imager in humans. Brain and behavior. Sep. 2016;6(9):e00530.
Schulz et al., Simultaneous assessment of rodent behavior and neurochemistry using a miniature positron emission tomograph. Nature Methods. Apr. 2011;8(4):347-52.

* cited by examiner

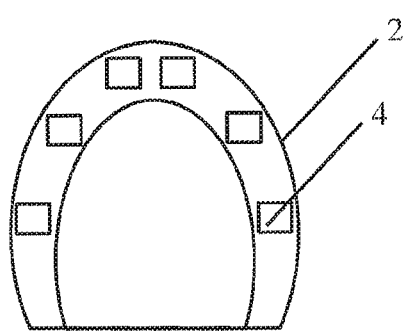
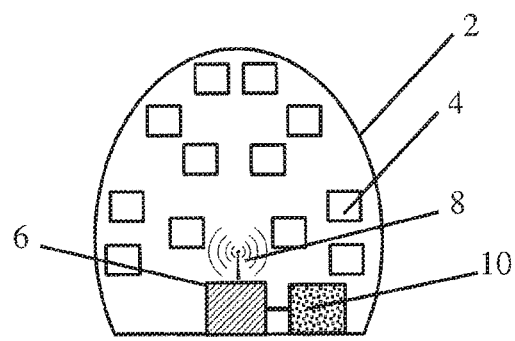
Fig. 1A    Fig. 1B
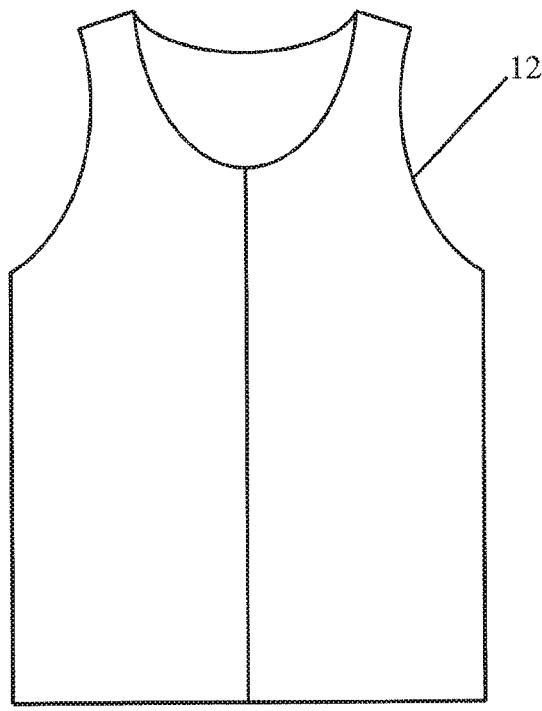
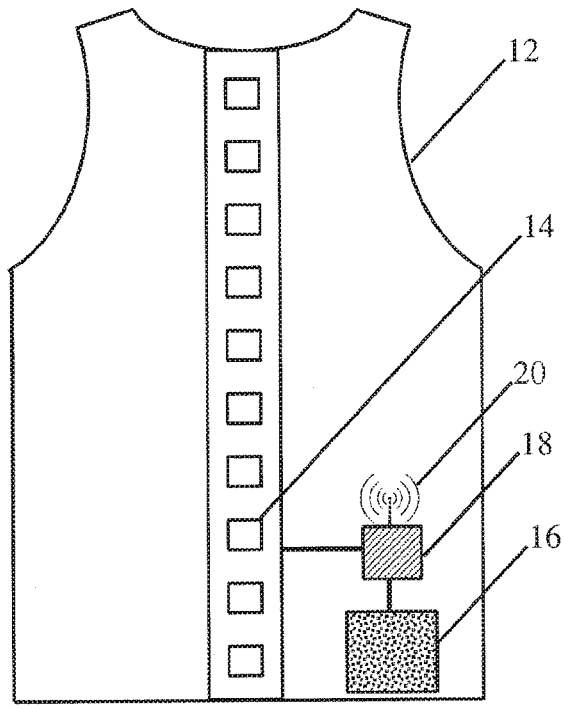
Fig. 2A    Fig. 2B

MEDICAL DIAGNOSTIC AND TREATMENT SYSTEMS AND THEIR METHODS OF USE

RELATED APPLICATIONS

This application is a National Stage filing under 35 U.S.C. § 371 of international application ser. no. PCT/US2017/062937, filed on Nov. 22, 2017, which claims the benefit of priority under 35 U.S.C. § 119(e) of U.S. provisional application Ser. No. 62/425,361, filed Nov. 22, 2016, the disclosures of each of which are incorporated herein in their entirety.

FIELD

Disclosed embodiments are related to medical diagnostic and treatment systems and their methods of use.

BACKGROUND

Medical imaging techniques that rely on detection of emissions from tracers originating from within the body of a subject are widely used for diagnosis of various diseases and other medically relevant applications. Nuclear physics-based molecular imaging techniques, such as positron emission tomography (PET) and single photon emission computed tomography (SPECT) allow imaging of subjects using radioactive isotopes. For example, SPECT is based on the use of radioisotopes that emit gamma rays and PET is based on the use of radioisotopes that emit positrons, which annihilate electrons to produce gamma rays. In contrast to nuclear imaging techniques, fluorescence based optical imaging techniques do not involve ionizing radiation such as gamma rays. Instead, fluorescence imaging relies on the excitation of fluorescent tracers by an excitation source that results in the absorption of photons by the fluorophores, and the subsequent detection of photons emitted by the fluorescent tracers as they decay from their excited state. A disadvantage of the various imaging techniques that rely on internal tracers, such as PET, SPECT and fluorescence imaging, is that they rely on the use of large scale and expensive scanners for the detection of emissions from these internal tracers, thereby requiring costly visits to radiology clinics.

SUMMARY

In one embodiment, a medical detecting system includes a wearable structure for wearing on a body portion of a subject. One or more radiation detectors are coupled to the wearable structure such that the one or more radiation detectors are positioned proximate to the body portion and distanced from a surface of the body portion of the subject when the wearable structure is worn by the subject. Additionally, the one or more radiation detectors detect radiation emitted from within the body portion.

In another embodiment, a method includes: positioning a wearable structure on a body portion of a subject, wherein positioning the wearable structure also positions one or more radiation detectors proximate to the body portion of the subject; maintaining a distance between the one or more radiation detectors and a surface of the body portion of the subject; and detecting radiation emitted from within the body portion using the one or more radiation detectors.

In yet another embodiment, a medical detecting system includes a wearable structure for wearing on a body portion of a subject and at least two radiation detectors coupled to the wearable structure such that the at least two radiation detectors are positioned at different radial positions relative to the body portion when the wearable structure is worn by the subject. The at least two radiation detectors detect radiation emitted from within the body portion.

In still another embodiment, a method includes: positioning a wearable structure on a body portion of a subject, wherein positioning the wearable structure also positions at least two radiation detectors at different radial positions relative to the body portion of the subject; and detecting radiation emitted from within the body portion using the at least two radiation detectors.

In another embodiment, a medical detecting system includes a wearable structure for wearing on a body portion of a subject and one or more radiation detectors coupled to the wearable structure such that the one or more radiation detectors are positioned proximate to the body portion when the wearable structure is worn by the subject. The one or more radiation detectors detect radiation emitted from within the body portion. Additionally, a compressive feature associated with the wearable structure restricts blood flow to the subject's skin proximate to the one or more radiation detectors when the wearable structure is worn by the subject.

In yet another embodiment, a medical detecting system includes a wearable structure for wearing on a body portion of a subject and one or more radiation detectors coupled to the wearable structure such that the one or more radiation detectors are positioned proximate to the body portion when the wearable structure is worn by the subject. The one or more radiation detectors detect radiation emitted from within the body portion. The system also includes a cooler associated with the wearable structure, where the cooler cools the body portion.

In still another embodiment, a method includes: positioning a wearable structure on a body portion of a subject, wherein positioning the wearable structure also positions one or more radiation detectors proximate to the body portion of the subject; reducing a flow of blood to at least a portion of the subject's skin proximate to the at least one detector; and detecting radiation emitted from within the body portion using the one or more radiation detectors.

In yet another embodiment, a medical detecting system includes a wearable structure including one or more flexible arms, where the wearable structure is wearable on a head of a subject. One or more radiation detectors are also disposed along a length of the one or more flexible arms. The system also includes one or more spacers associated with the one or more flexible arms, where the one or more spacers are disposed between the head of the subject and the one or more radiation detectors when the wearable structure is worn by the subject.

In another embodiment, a method includes: positioning one or more flexible arms of a wearable structure on a head of a subject, wherein one or more radiation detectors are disposed along a length of the one or more flexible arms; positioning one or more spacers between the head of the subject and the one or more radiation detectors; and detecting radiation emitted from within the body portion using the one or more radiation detectors.

In still another embodiment, a method includes: administering a labeled compound including a radioactive tracer to a subject; detecting a radiation signal that varies over time and is emitted from a body portion using one or more radiation detectors over a predetermined time period; outputting the detected radiation signal to a computing device; analyzing the radiation signal with the computing device to determine one or more signal characteristics of the radiation signal during the predetermined time; and using the computing device to compare the one or more determined signal characteristics to one or more standard characteristics to determine a treatment and/or disease state of the subject.

In yet another embodiment, a medical detecting system includes: one or more radiation detectors that detect a time varying radiation signal emitted from a body portion and a computing device in communication with the one or more radiation detectors. The one or more radiation detectors output the detected radiation signal to the computing device. Further, the computing device analyzes the radiation signal to determine one or more signal characteristics of the radiation signal during a predetermined time. The computing device then compares the one or more determined signal characteristics to one or more standard characteristics to determine a disease state and/or treatment state of the subject.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 1A is a schematic front view of a helmet including a plurality of detectors;

FIG. 1B is a schematic rear view of the helmet of FIG. 1A;

FIG. 2A is a schematic front view of a vest including a plurality of detectors;

FIG. 2B is a schematic rear view of the vest of FIG. 2A;

DETAILED DESCRIPTION

Figure 3:
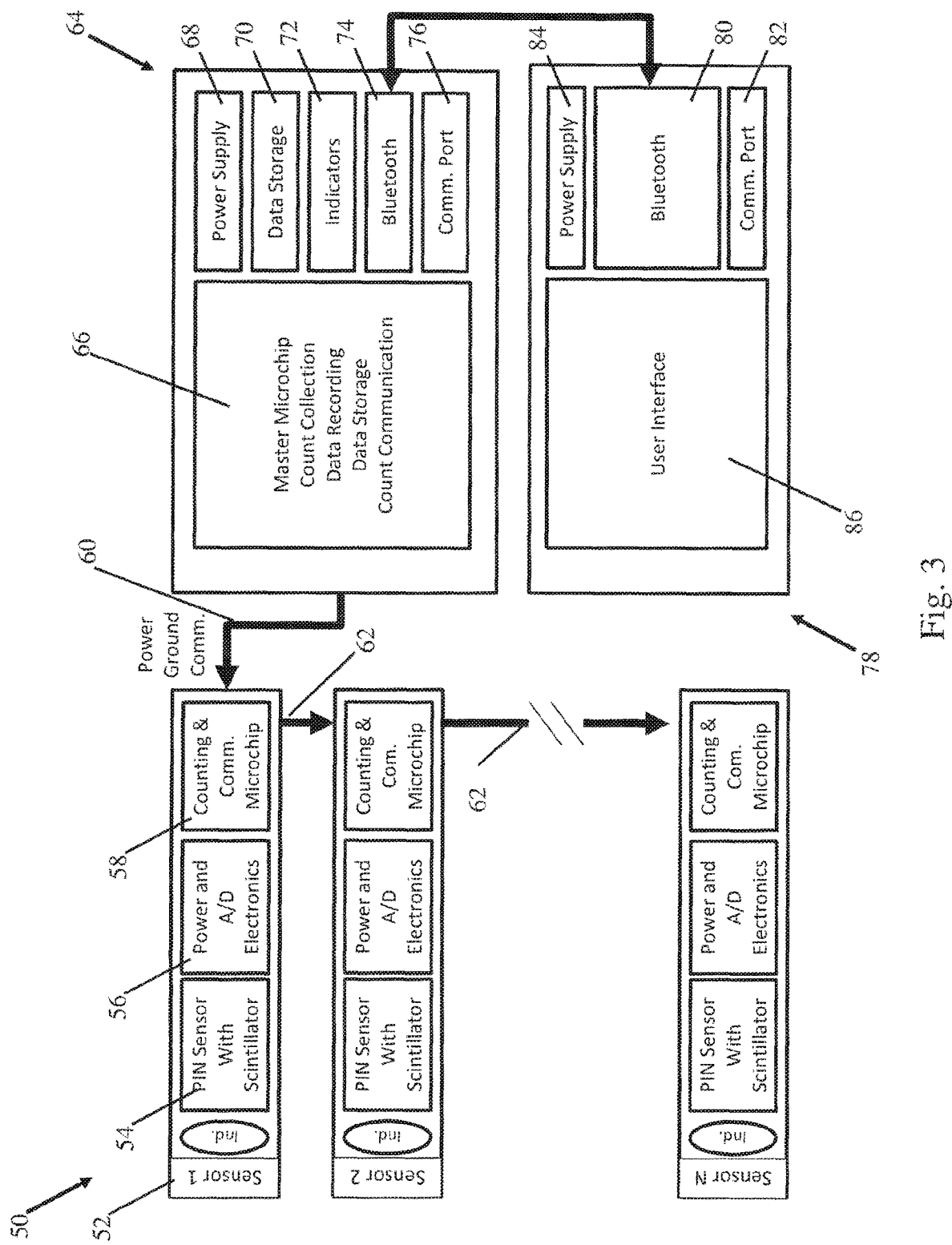
FIG. 3 is a schematic representation of a device including a plurality of detectors, a controller, and an associated computing device.

In view of the expense and inconvenience associated with the use of large scale detectors often found in radiology labs, the inventors have recognized the benefits associated with wearable and/or mobile detectors for monitoring the presence, concentration, and/or changes over time of one or more tracers within one or more body portions of a subject. Specifically, the inventors have recognized the benefits associated with a medical detecting system including a wearable structure that may be worn on a portion of a subject's body for detecting radiation emitted from within that body portion for either diagnostic and/or treatment purposes.

In one embodiment, a medical detecting system may include a wearable structure for wearing on a body portion of a subject. To enable detection of a radioactive tracer associated with a labeled compound, the system may also include one or more radiation detectors attached to the wearable structure. The radiation detectors may be integrated into the wearable structure so that they are positioned proximate to, and distanced from a surface of, the body portion of the subject when the wearable structure is worn. For example, in one specific embodiment, one or more spacers may be disposed either directly, or indirectly, between a body portion of the subject and the radiation detectors when the wearable structure is worn by the subject.

In some embodiments, in addition to detecting a radiation signal emitted from a body portion, such as the head, it may be desirable to reduce and/or compensate for a radiation signal emitted from the skin associated with that body portion. This may be done in a number of ways detailed further below. For example, in one particular embodiment, two or more detectors may be positioned at different radial positions relative to the body portion to permit the two separate signals from the body portion of interest and the skin to be deconvolved with one another by taking and comparing signal measurements at the different radial positions as described further below. In another embodiment, a wearable structure may include one or more compressive features that restrict a flow of blood to the portions of the skin proximate to the detectors to reduce the amount of a labeled compound from reaching the skin. In yet another embodiment, a cooler may be used to cool the skin of the body portion associated with the detectors to again reduce a flow of blood, and an associated labeled compound, to the skin.

Using the systems described herein, or any other appropriate medical detection system capable of monitoring radiation emitted from a body portion, it may be possible to correlate the detected radiation signal with a particular disease state and/or treatment state of a subject. In such an embodiment, a labeled compound including a radioactive tracer may be administered to subject in any appropriate manner including, but not limited to: infusion; injections such as intramuscular injection, intravascular injection, and/or subcutaneous injection; orally ingested; inhalation; or any other appropriate method of administering a compound to a subject. Following administration of a labeled compound, one or more radiation detectors may be used to measure a time varying radiation signal emitted by one or more associated body portions. This detected signal may be output to, and analyzed by, a computing device to determine one or more signal characteristics that characterize variations in the radiation signal during the predetermined time period. Depending on the embodiment, these signal characteristics may then be used to either determine a disease state and/or a treatment state of the subject by comparing them to standard signal characteristics associated with known disease states and/or treatment states. For example, in one embodiment, a labeled compound may be a labeled radioactive probe that targets a particular disease characteristic, e.g. a probe including a ligand that targets a protein of interest, e.g., a cell-associated protein (e.g., a tumor cell or an immune cell), a soluble protein (e.g., a neurotransmitter), a fibrillary protein (e.g., beta amyloid present in the brain), such that the presence or absence of a signal, or a signal exhibiting particular characteristics, indicates that the subject likely does or does not have a particular disease state. Alternatively, in another embodiment the labeled compound may be used to either treat a known disease state and/or maintain a physical characteristic of the subject by controlling a desired concentration, location, timing, dosage, and/or rate of delivery of the labeled compound to the subject from an associated treatment device. Both of these embodiments, as well as variations of these embodiments, are described further below.

For the sake of convenience, the embodiments described herein are described relative to medical detecting systems that use a plurality of detectors for sensing radiation signals emitted from one or more portions of a subject's body. However, it should be understood that the systems and methods described herein are not limited to uses involving only multiple detectors. Instead, it should be understood that the systems and methods described herein may be used with any number of detectors including a single detector associated with a single body portion. Further, the various described embodiments may be used with detectors that are repositionable or they may be used with systems where the detectors are maintained in fixed positions within the system. Additionally, embodiments in which a medical detecting system includes both one or more detectors that are fixed in position and one or more detectors that are repositionable are also contemplated as the disclosure is not limited in this fashion.

In addition to the above, for the sake of clarity and convenience, specific applications of medical detecting systems for monitoring the presence, concentration, and/or changes over time of a tracer within certain portion of a subject's body, such as the head, are described herein. However, in some embodiments, it may be desirable to have a medical detecting system that monitors the presence, concentration, and/or changes over time in the presence or concentration of a tracer within other portions of the body as well. Further, depending on the particular embodiment, a wearable structure including the attached detectors may correspond to any number of different arrangements for wearing on different body portions. For example, the wearable structure may take the form of a hat, helmet, chin strap, vest, shirt, cap, shoe, glove, bracelet, sleeve, legging, sock, stocking, collar, head band, arm band, leg band, waist band, shorts, pants, body sleeve, corset, eyeglasses, headphone, exoskeleton, frame, or any other appropriate structure. Embodiments in which an exoskeleton and/or frame form at least a portion of a wearable structure may correspond to any appropriate configuration of a rigid structure that is capable of being worn on a portion of a subject's body. This may either correspond to a shell or cage like structure, or a portion of a rigid component or frame may be attached to another wearable structure including those noted above.

While multiple individual wearable structures have been described above, in some embodiments, a combination of two or more separate structures corresponding to any of the foregoing wearable structures may be worn by a subject to permit monitoring radiation signals emitted from either one or a plurality of body portions at the same time. Alternatively, in some embodiments, two or more of the above noted wearable structures may be combined into a single wearable structure. For example, a wearable structure may include a shirt, collar, and/or hat combined in a single structure, though other combinations are also envisioned.

In view of the above, in some embodiments, a wearable structure may either be a flexible and/or stretchable material such as a fabric, or it may be in the form of a rigid shell or frame made from a material such as a bulk plastic or metal, tubes, bars, or any other appropriate form factor. The structures may also be attached to an associated body portion using any appropriate method including, for example, the inherent elasticity of a material, straps, elastic bands, snap connectors, buttons, ties, zippers, touch fasteners, clips, adhesives, magnets, interference fit, and/or any other applicable method of attaching and/or fitting the structures to a related body portion and/or to clothing or a structure worn on a body portion. Additionally, in instances where a system is integrated with a garment, the various detectors, traces, and other appropriate electronics, may be integrated with the garment using wearable circuitry, though other arrangements are also possible. In view of the above, it should be understood that the systems and methods described herein may be used with any appropriate body portion, and should not be limited to only being used with a subject's head.

The currently disclosed systems may be applied to measure the presence, concentration, and/or changes over time in the presence or concentration of tracers within distinct portions of a subject's body. This can allow optimized tracking of very low signals by placing detectors appropriately on portions of the body close to the locations of interest. For example, appropriate body portions include, but are not limited to, the head, torso, abdomen, arms, hands, hips, legs, ankles, feet, neck, combinations of the above, and/or sub portions of these body portions. Further, detectors located on these body portions may be used for monitoring the presence, concentration, and/or changes over time in the presence or concentration of a labeled compound within a thyroid, lymph node, salivary gland, eye, deep vein, brain, intrathecal space of the spine, appendix, liver, kidneys, adrenal glands or other appropriate structure of a subject's body.

In one embodiment, one or more detectors may be arranged along a subject's spine and/or head for monitoring a labeled compound within the intrathecal space and/or brain of a subject. In embodiments where the detectors are arranged around a subject's head, the detectors may have enclosures with a hexagonal cross section, or other appropriate shape, to enable the detectors to be placed adjacent to one another with the enclosures in contact and arranged in a partial icosahedron or other appropriate shape. The resulting shape may approximate a partial sphere encompassing a subject's head. However, embodiments in which the detectors are simply arranged in a desired layout without any associated enclosures being in contact with one another are also contemplated. In another embodiment, one or more detectors are arranged proximate to a subject's neck for measuring tracers in a thyroid and/or neck lymph nodes of a subject when the device is in a worn by the subject. Alternatively, in another embodiment, one or more detectors are arranged proximate to the face cheeks, chin, and/or neck of a subject to measure salivary gland uptake when the device is in a worn by the subject. In yet another embodiment, detectors are arranged proximate to the arm pits and/or groin of a subject for detecting tracers located in the related lymph nodes located in those portions of the body when the device is in a worn by the subject. In another application, a system is designed for monitoring the appendix of a subject and thus includes detectors worn over a right lower quadrant of a subject's torso. Other possible applications include a wearable structure intended to be worn over the calves in the form of a stocking, or similar form, with one or more detectors for monitoring deep vein thrombosis using a tracer, such as a Procrit tracer. Detectors may also be used to monitor the presence, concentration, and/or changes over time in the presence or concentration of tracers adjacent and/or in the eyes of a subject. In such an embodiment, an eyepatch, or similar structure, may be positioned over the eye with one or more detectors to enable the detection of relatively small signals which may aid in detecting drug concentrations, gene expression, and/or biomarkers in age-related macular degeneration (AMD) or other eye disorders.

In view of the above, it should be understood, that the presently disclosed systems may be integrated into any number of different wearable structures and may be used for monitoring signals emitted from any number of different body portions of a subject as the disclosure is not so limited. Additionally, as detailed further below, embodiments in which a medical detecting system detects signals from multiple labeled compounds administered to a subject at the same time are also contemplated.

It should be understood that any appropriate tracer may be used with the presently disclosed systems. For example, a tracer associated with a particular compound of interest may be a radioactive tracer such as a radioactive isotope. Appropriate radioactive isotopes include, but are not limited to, $^{11}C$, $^{13}N$, $^{22}Na$, $^{18}F$, $^{15}O$, $^{131}I$, $^{123}I$, $^{124}I$, $^{125}I$, $^{111}In$, $^{57}Co$, $^{60}Co$, $^{61}Cu$, $^{64}Cu$, $^{67}Cu$, $^{67}Ga$, $^{188}Re$, $^{99m}Tc$, $^{201}Tl$, and $^{137}Cs$, or any other appropriate isotope. Appropriate detectors for detecting a radioactive tracer include, but are not limited to: scintillating materials coupled with a PIN diode, a CMOS camera, and/or a CCD camera; direct conversion devices (i.e. solid state radiation detectors) such as CdZnTe semiconductor detectors; Geiger-Mueller tubes; or any other appropriate detector capable of detecting a radiation signal. While detectors capable of outputting a detected radiation signal have been disclosed above, embodiments in which analogue film is positioned within the detectors to detect the noted radiation signals are also contemplated. In such an embodiment, after exposure, the film may be removed, developed, and analyzed to determine the radiation counts associated with each detector. These determined radiation signals may then be used similar to any of the other radiation signals discussed herein. Accordingly, it should be understood that the current disclosure should not be limited to any particular type of detector or method for detecting a radiation signal.

For purposes of this disclosure, the term wearable may include a structure capable of being worn or carried on the body of an individual similar to an item of clothing, exoskeleton, frame, or any other structure capable of being worn by a subject. Depending on the particular embodiment, the wearable device may provide freedom of movement for a subject wearing the systems due to the use of wireless connections, visual indicators, a power source (e.g. batteries, capacitors, wireless power transmission, etc.), and/or storage for later download of detected information. However, embodiments in which a medical detecting system includes one or more wearable structures, has a wired connection to a controller and/or storage device, or otherwise limits the movement of a subject are also contemplated as the disclosure is not so limited.

Labeled compounds for purposes of this application may correspond to any appropriate material including, but not limited to, any drug, medication, pharmaceutical preparation, contrast agent, and/or biologic such as a protein, antisense molecule, and gene therapy viral vector as the disclosure is not so limited. Further, a tracer or probe associated with a labeled compound may be bonded to the labeled compound using any appropriate method known in the art. It should be understood that the specific amount and effect will vary depending on the particular labeled compound being used. Additionally, as will be appreciated by one of skill in the art, the labeled compounds described herein may be provided in any number of different forms including, but not limited to, suspensions, liquids, slurries, powders, aerosols, nanoparticles, and/or gels. When a labeled compound is present in a particular location in an "effective amount" it means a concentration of the labeled compound is greater than or equal to a trace amount and is sufficient for achieving a desired purpose, such as, for example, to permit detection of the labeled compound in a subject for diagnostic purposes, to treat a disease or condition in a subject, and/or enhance a treatment of a disease or condition in a subject. In some embodiments, an effective amount of a particular labeled compound is present in an amount sufficient to reduce or alleviate one or more conditions associated with a particular condition (e.g., neuropathic pain, primary brain or metastatic cancer, neurodegenerative disease, neurogenetic disease, neuro-infections).

In view of the above, it should be understood that a labeled compound may correspond to any appropriate compound that may be administered to a subject. However, in one embodiment, a labeled compound is a therapeutic compound used to treat one or more conditions. In another embodiment, a labeled compound is a diagnostic compound such that its presence, or absence at a particular location is indicative of a particular condition.

As noted previously, the labeled compounds described herein may be conjugated with a detectable moiety to enable the presently described detectors to detect their presence. For example, a detectable moiety may be a radioisotope as described previously. It should be noted that in the case of radioactive tracers, the tracers selected for a particular application and duration of monitoring may have a sufficiently long half-life to provide a detectable signal throughout the monitoring period. Due to different tracers having different half-lives, one of skill in the art may select an appropriate tracer based both on its ability to be conjugated with a compound as well as its half-life versus the time period monitoring will be conducted over. Additionally, as detailed further below embodiments in which multiple labeled compounds including different detectable moieties may be administered to a subject as the disclosure is not limited in this fashion.

Based on the above, it should be understood that a medical detecting system as disclosed herein may be used for any number of applications. In one embodiment, a medical detecting system may be used to detect the presence, absence, concentration, and/or changes over time of a labeled compound within a particular body portion. As noted above, this may either correspond to the detection of a therapeutic compound being delivered to a desired location and/or the presence or absence of a particular condition in a body portion such as the presence or absence of a particular type of protein (e.g. beta amyloid) in the brain. In one such embodiment, the labeled compound is a diagnostic compound conjugated with a detectable moiety, as noted above, such that its presence and/or concentration as detected by the medical detecting system may be used to identify a medical condition such as a particular disease state. Alternatively, in another embodiment, a labeled compound may be used to treat a particular condition. Therefore, in one embodiment, a medical detecting system may be used to detect the presence, concentration, and/or changes over time of the labeled compound to either insure that an effective amount of the labeled compound has reached the target location, that an effective amount of the labeled compound is maintained during a treatment period, and/or that treatment should continue until an effective amount of the labeled compound has reached the target location. For example, a medical detecting system may include detectors distributed along both a spine and/or about the head of a subject such that the detectors may monitor the progress of a labeled compound as it disperses from an administration site along the intrathecal space and into the brain tissue of a subject. Of course, while several possible applications are detailed herein, it should be understood that other applications for the presently disclosed medical detecting systems are also contemplated as the disclosure is not limited to any specific application.

In one specific embodiment, a medical detecting system may be included in a wearable structure that is worn on the head of a subject. Such a system may be used for detecting and/or monitoring the treatment of different disease states associated with the head. Generally, by using appropriate labeled compounds with appropriate tracers, a medical detecting system may be used to measure lesions, physiology, synapses within a subject's brain, and/or other appropriate conditions. In one such embodiment, various types of labeled compounds may be used to measure the metabolic and vascular health state of the brain of a subject including radiolabeled blood perfusion agents, metabolic fuels such as glucose, lipids and ketone bodies. For example, blood flow monitoring may be conducted using an appropriate compound and tracer to enable detection of conditions such as a stroke or an aneurism. In another embodiment, a Schizophrenia diagnosis may be accomplished using tracers that target dopamine receptors. In yet another embodiment, it may be desirable to detect proteins associated with particular conditions. In such an embodiment, a labeled compound may target beta-amyloid, alpha-synculein, tau, TDP43, other pathological protein and RNA intracellular inclusions, inflammation, tumors, and other appropriate features. In one specific example, amyloid plaques present in the brain may be targeted. In yet another embodiment, labeled compounds may be used for quantifying total and specific subtypes of synapses. Appropriate probes may target protein components found in all synapses (such as synaptic vesicle associated proteins) which may be used to track overall synaptic content while receptor specific probes that target subtypes of synapse such as dopaminergic, serotoninergic, GABAergic, glutamatergic and others may be used quantify these parameters as useful brain health biomarkers.

It should be understood that any appropriate imaging technique may be used with the systems and methods described herein. However, in some embodiments, appropriate arrangements and types of detectors with sufficient sensitivities and/or timing precision capabilities may be used to enable imaging techniques such as PET, SPECT and/or any other appropriate detection technique. These detection techniques may then be used to measure the presence of a labeled compound within discrete portions of a subject's body. For example, by placing detectors directed at one or more regions of interest within a body portion, it may be possible to detect activity in desired sub-regions within a body portion of interest, such as the head. Thus, a medical detecting system may be used to identify regions with different concentrations of a labeled compound. Further, in some embodiments, it may be desirable to increase a number of detectors directed towards a particular region of interest to provide increased sensitivity and/or resolution for signals emitted from the region of interest. While such a capability may be used for determining a treatment and/or disease state of a subject, in some embodiments, a medical detecting system may also be used to quickly and cheaply evaluate the affinity particular labeled compounds have for different anatomical structures. This may be of benefit when developing compounds to target specific portions of a subject's body for treatment and/or diagnostic purposes.

In one embodiment, the above described methods for detecting regions of activity within a body portion may be used for metabolism measurements. For example, $^{18}$F-FDG may be administered for brain glucose metabolism and/or $^{99m}$Tc-HMPAO targeted by a labeled compound may be administered for measuring regional brain blood flow. In addition to the above, the overall signals and regional heterogeneity of emitted signals from within the head of a subject for some labeled compounds varies in conditions like neurodegeneration diseases such as: Alzheimer disease and frontotemporal dementia which exhibit different regional brain pattern loss with both FDG and HMPAO; stroke; trauma; coma; and brain death. Therefore, emitted signals may be analyzed to determine overall signals and heterogeneities for determining certain conditions as well.

In yet another embodiment, synapses may be monitored using PET and/or SPECT ligands that target unique synapses (e.g. Dopamine with 123I-Ioflupane; GABA with 123I-Iomazinol, Acetylcholine, serotonin, etc.). The devices and methods described herein may then be used to quantify major synapse types in the brain conveniently which may be used to determine population norms for these brain numbers. Further, decline in synapse numbers occurs gradually with aging but rapidly with neurodegeneration which may be used to detect the onset of this type of disease state.

In addition to the specific applications noted above, the currently disclosed devices and methods may be used to monitor both the above noted conditions, and other applicable conditions as the disclosure is not limited to detecting any particular subject state or probe.

Turning now to figures, several specific embodiments are described in further detail. For example, medical detecting systems including detectors for detecting the presence, concentration, and/or changes over time of labeled compounds within the head are primarily described. However, it should be understood that systems including other wearable structures and/or detectors located adjacent to other body portions are also contemplated as previously described. Consequently, the present disclosure should not be limited to only the embodiments described in the figures and should instead be interpreted broadly as encompassing any of the systems, features, and/or combinations of these various embodiments described herein as the disclosure is not so limited.

FIGS. 1A-2B depict embodiments of two different medical detecting system including two separate wearable structures corresponding to a cap 2 wearable on a head of a subject and a vest 10 wearable on a torso of the subject. The functionality of the cap and the vest which include one or more radiation detectors are described further below.

The depicted cap 2 of FIGS. 1A-1B includes a plurality of detectors 4 distributed around and coupled to the cap to measure the presence, concentration, and/or changes over time of a tracer within different locations of the brain of a subject wearing the cap. The cap also includes one or more controllers 6 in communication with the detectors 4 to readout the counts and/or images provided by each detector. Depending on the particular embodiment, the controller may either simply read out a signal provided by the detectors, or it may also control the collection and timing of signals from the detectors, as the disclosure is not limited to any particular type of control scheme for the detectors.

The exemplary embodiment of a vest 12 depicted in FIGS. 2A and 2B is a simple construction that may either be slipped on the torso of a subject and/or the vest may include an openable seam for easily donning the garment by a subject. To close the openable seam, the vest may include appropriate closure mechanisms such as straps, elastic bands, snap connectors, buttons, ties, zippers, touch fasteners, clips, adhesives, magnets, interference fits, and/or any other applicable attachment method, not depicted. While a vest with an openable seam has been depicted, other appropriate structures for wearing on a torso of a subject may also be used.

As illustrated in the figures, a vest 12 may also include one or more detectors 14 coupled to the structure for detecting the presence, concentration, and/or changes over time in the presence or concentration of a tracer within the intrathecal space of a spine of a subject. In one such embodiment, a plurality of detectors are distributed along the spine of the subject, as illustrated in FIG. 2B. Similar to the cap, the vest 12, or other similar wearable structure, may also include a controller 18 in electrical communication with the one or more detectors 16 of the vest in order to readout the signal detected by each of the detectors as well as possibly controlling the detectors as noted previously.

While the above described detectors have been depicted as being coupled to an exterior surface of the associated wearable structures, the current disclosure is not so limited. Instead, the presently disclosed detectors may be coupled to a structure such that they are disposed on an interior surface, exterior surface, within the wearable structure, or at any other appropriate location relative to the wearable structure.

To enhance mobility as well as provide for possible smart functionality, it may be desirable to provide a wireless connection for remotely controlling the detectors and/or downloading information received from the various detectors. In such an embodiment, a transmitter 8 associated with the cap and/or a transmitter 20 associated with the vest are in electrical communication with their respective controllers 6 and 18 as well as the associated detectors. Therefore, images and/or counts corresponding to detected signal emissions from at least one tracer located in a portion of the body may be transmitted by the one or more depicted transmitters to a separate computing device such as a server, computer, tablet, smart phone, and/or any other appropriate device. In some embodiments, the computing device is a remotely located computing device. For example, in one such application, information may be transmitted from a medical detecting system to a cloud-based storage server and/or to another database or system accessible by medical personal overseeing a medical condition or procedure for the subject being monitored by the medical detecting system. Alternatively, or in addition, onboard computer memory such as flash memory, EEPROM memory, solid-state memory, or any other appropriate memory device may be used to store information from the one or more detectors for subsequent download by a physical link as the disclosure is not so limited. It should be understood that while transmitters associated with the individual controllers located on the separate structures has been depicted in figures, in other embodiments, a transmitter located on a wearable structure may be in communication with detectors located on another separate wearable structure either via a hardwired or wireless link such that the transmitter is capable of transmitting information related to both sets of detectors located on the separate wearable structures to a separate computing device. Of course, embodiments in which the computing device is incorporated into one or more of the wearable structures are also contemplated.

In some embodiments, a medical detecting system is intended to be used in a mobile application. In such an embodiment, a system may include one or more batteries. Depending on the embodiment, one or more batteries such as battery 10 associated with the cap 2 and battery 16 associated with the vest 12 may be used to power the controllers, transmitters, and/or detectors of the various wearable structures for sensing a signal emitted from within a portion of a subject's body. Of course, embodiments, in which individual batteries are not included in each wearable structure are also contemplated. In such an embodiment, an electrical connection may extend between two or more separate wearable structures to provide power to the corresponding controllers, transmitters, and/or detectors. However, it should be understood that batteries may be positioned at any region of a structure as well as on wearable structures worn on other portions of a subject's body other than their head and/or torso as the disclosure is not so limited. Further, all of the depicted components including the detectors, controller, transmitter, and/or battery may be located outside, inside, and/or within a wearable structure as well.

The above embodiments have been directed to medical detecting systems including a plurality of stationary detectors. However, it should be understood that the current disclosure is not limited to uses including only a plurality of detectors permanently attached to specific portions of a medical detecting system. Instead, the current disclosure also includes embodiments in which a wearable structure includes a single detector, and/or multiple detectors, that may be repositioned on a wearable structure. Thus, in some embodiments, a single detector, and/or any number of detectors, may be movable and selectively attached at different locations relative to a wearable structure they are integrated with. For example, a wearable structure may include attachment points and/or fastening material that a corresponding mating attachment and/or material associated with a detector may be selectively mated with to selectively attach the one or more detectors at any one of a plurality of locations on the wearable structure. For example, in one embodiment, a plurality of attachment points may be distributed about the surface of the wearable structure. A corresponding attachment structure located on the one or more detectors may then be used to selectively attach the one or more detectors thereto. Appropriate types of attachment include, but are not limited to, hook and loop materials, mating portions of snap fasteners, interference fits, adhesives, holes and buttons, or any other appropriate attachment method as the disclosure is not so limited.

FIG. 3 depicts one embodiment of an electrical layout of a medical detecting system 50. In the depicted embodiment, the system includes a plurality of detectors 52, a controller 66, and an associated computing device 78. Each of the detectors in the depicted embodiment include a PIN detector coupled with a scintillator such that the detectors are capable of detecting incident gamma rays and/or other appropriate forms of radiation. The PIN detectors are in electrical communication with electronics 56 that supply power to the detector and convert the resulting analog signal to a digital signal for subsequently outputting to the controller. The electronics 56 are in electrical communication with a counting and communication microchip 58. The microchip 58 may be in electrical communication with the counting and communication microchip of other associated detectors via electrical connections 62 and/or with a primary controller 66 via electrical connection 60. Thus, the detectors may be able to communicate signals to the primary controller either through a daisy chain configuration as depicted in the figure, or in other embodiments, individual connections may be made between the individual detectors and the controller as the disclosure is not so limited. Additionally, while a wired connection has been depicted in the figures, wireless communication between the detectors and controller may also be used. Further, depending on the particular embodiment, the individual detectors may communicate with the controller using any appropriate wired protocol, such as I2C, and/or wireless communication protocol, such as Bluetooth, NFC, or WLAN. In the case of wireless communication each detector may locally store data that can be asynchronously passed to the controller during one or more communication periods.

To help conserve power, in some embodiments, the detectors of a medical detecting system may optionally be operated in low power mode to save power when continuous readings are not necessary. The device may also automatically turn off when the detectors do not sense any activity for an extended period of time.

Depending on the type of procedure being performed, the specific labeled compounds being used, and/or the specific type of tracer being used, it may be desirable to alter a mode of operation of the one or more detectors to alter their detection characteristics. For example, in one embodiment, in a first mode of operation a controller and/or switch associated with the one or more detectors of a system may selectively apply a high reverse voltage across the one or more PIN diodes to provide a higher maximum count and/or sensitivity at the expense of higher detected noise which may be appropriate when high amounts of activity are sensed in one mode of operation. Alternatively, in a second mode of operation, the controller and/or switch may apply a lower reverse voltage to the PIN diodes to provide lower maximum counts and lower noise which may be appropriate for low levels of sensed activity. This switching capability between the high and lower reverse voltages may either be discrete (i.e. high or low) or the voltage may be varied continuously between the upper and lower voltages (i.e. sweep voltage range). Additionally, in some embodiments, the applied voltage may be controlled digitally based on the detected count rate. In one such embodiment, a controller may selectively operate the detectors in the lower reverse voltage mode when a signal count is below a threshold signal count and may operate the detectors in the higher reverse voltage mode when the signal count is above the threshold signal count. In addition to the above, in some embodiments, a controller may also apply dead time correction for each voltage level.

As also shown in FIG. 3, a controller 64 may include a number of different electrical components including, for example, a processor 66 and memory 70. The processor may be used to perform count collections, data recording, data analysis, transmitting data to an associated memory for data storage, and/or initiating communication of the recorded counts from the detectors as detailed further below. While any appropriate type of memory may be used, in one embodiment, the processor may be in electrical communication with a stable memory 70 such as a hard drive, an SD-card, EEPROM, other forms of solid state memory, and/or any other appropriate form of memory. Further, depending on the particular embodiment, the memory may either be permanently attached to the controller and/or it may be removable in some embodiments.

In addition to the above, a controller 66 may be in electrical communication with a power supply 68 such as a battery which may be located at any appropriate location on the medical device. For example, in one embodiment a system may use a coin cell battery attached to a cap the detectors and controller are integrated with. Further, the battery may either be used for multiple sessions and/or a fresh battery may be inserted into the system before each session. While a system including a battery has been described above, embodiments in which an external power source may be used are also contemplated as the disclosure is not so limited. In one such embodiment, the system may plug into an electrical outlet, a generator, an external power supply, and/or any other appropriate source of power.

In some embodiments, a controller 64 may also include one or more indicators 72 that are in electrical communication with a processor 66 of the controller in order to communicate one or more forms of information to a user or subject. The indicators may correspond to one or more light emitting diodes, other types of light sources, bistable display components, a touch screen, a display, or any other type of way to indicate information to a user and/or subject. These indicators may indicate if the system is operating, if a signal has been detected, and/or if a fault (e.g. a non-functional detector) has been detected using any appropriate method including but not limited to color changes, intensity changes, icons, and/or lighting up an icon to name a few.

To enable free mobility of a subject, in some embodiments, a controller may also include a wireless transmitter 74, such as a Bluetooth communicator, or other transmitter as described previously, that is in electrical communication with the processor for communicating with the one or more detectors 52 and/or the associated computing device 78. Further, in some instances the controller may also include a hard communication port 76 to permit wired communication and/or control to be established with the controller.

As indicated in the figure, a controller 66 may be in wireless communication with an associated computing device 78 via a blue tooth communicator 74 on the controller and a blue tooth communicator 80 on the computing device. The computing device may also include a power supply 84 to permit mobile and/or wireless applications as well as a user interface 86 such as a touch screen display, a display and associated keyboard or other input device, or any other appropriate configuration. The user interface may be used both to display information and to input subject specific parameters such as, but not limited to, body weight, height, race, dexterity, skull/hair circumference, detector position, patient name, date of birth, imaging time, and/or other testing results or diagnoses. Additionally, while the depicted computing device and user interface have been depicted as being separate from the system, embodiments in which the computing device and/or user interface are integrated into the medical detecting system are also contemplated as the disclosure is not so limited. The computing device may also include a hard communication port 82 to permit wired communication and/or control of the computing device. In one embodiment, the computing device is a portable computing device such as a tablet, smart phone, or any other appropriate device capable of communicating with and/or controlling the associated system.

Figure 4:
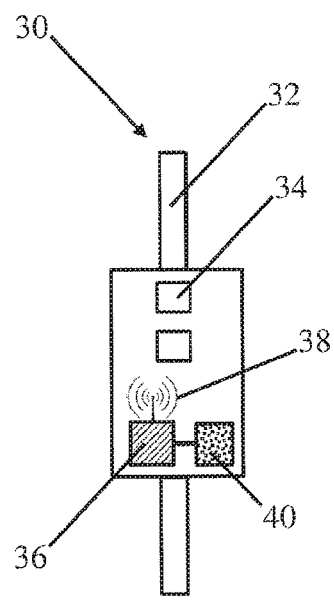
FIG. 4 is a schematic representation of a medical detecting system including a plurality of detectors for wearing around a body portion.

In some applications including, for example, monitoring of the pharmacokinetics of a compound conjugated with a tracer, it may be desirable to normalize a signal detected by one or more reference detectors associated with a given body portion to account for signal counts arising from compounds located within the blood as compared to the tissue of a particular body portion. In one such embodiment, the detected signals may be normalized using the signal detected at an extremity of a subject's body which is removed from the location of interest. Appropriate extremities include, but are not limited to, an ankle, wrist, arm, leg, or any other appropriately located portion of a body removed from an area of interest. One such device is shown in FIG. 4 which depicts a wearable structure in the form of a bracelet 30. The bracelet includes a pair of straps 32 that are selectively attachable to one another using any appropriate form of coupling such as a snap connectors, buttons, ties, zippers, touch fasteners, clips, magnets, and/or any other applicable method. Using these straps, the device may be attached to an extremity of the body such as the wrist or ankle a subject. Similar to the other wearable structures including detectors described above, the bracelet may include one or more detectors 34 for sensing the presence, concentration, and/or changes over time of one or more tracers as well as a controller 36, optional transmitter 38, and battery 40, the operations of which are described above.

A tracer signal detected from an extremity of a subject may be used to normalize detector signals in any number of ways. In the simplest embodiment, a signal from the reference detector is simply subtracted from the signals from the other detectors. In another embodiment, the signal corresponding to a tracer within the blood of the extremity may be scaled by the ratio of the blood volumes located in the extremity and location of interest. The scaled signal may then be subtracted from the signals of the other detectors. Depending on the particular embodiment, normalization of a signal may take into account different considerations. For example, normalization of a signal may be done using a baseline established for: a resting state; various states of activity (low, moderate, intense, etc.); or when a particular stimulus (e.g. vibrations, massage, electrical impulses, etc.) is applied to a subject. Additionally, these baselines may be established either relative to: a general population; a particular subject's physical characteristics relative to corresponding populations (e.g. age, height, weight, gender, ethnicity, etc.); a particular subject's baseline established over time and/or prior to a particular treatment; and/or any other appropriate consideration as the disclosure is not so limited. Of course, it should be understood that other techniques for normalizing a signal may also be implemented as the disclosure is not so limited. Normalization of the signal may also take into account background radiation which may be detected either with a separate detector, and/or the detector described above located on an extremity of a subject.

In the above embodiments, the use of wireless transmitters have been described for use with the presently disclosed medical detecting systems. However, the disclosure is not limited to only wireless transmitters. For example, hardwired connections to one or more of the wearable structures including detectors may also be used. Further, in some instances it may also be desirable to include a receiver in communication with the controller of a medical detecting system for receiving uploaded information such as commands from an externally located processing device such as a computer or server, time information, location information, or any other information that may be of use with a medical detecting system. For example, commands communicated back to the controller of a detector system may include altering the active versus inactive state of the detectors (i.e. turning the detectors on and off), adjusting measurement thresholds, applying signal filters, altering measurement frequency, altering measurement parameters (e.g. integration time), controlling the state of a detector mounted indicator, and/or any other appropriate control parameter for controlling the use of a medical detecting system. While in some instances a separate receiver may be used, in other embodiments, the described transmitters above may act as both transmitters and receivers as the disclosure is not limited to how transmission and reception of signals is specifically implemented on a device.

Figure 5:
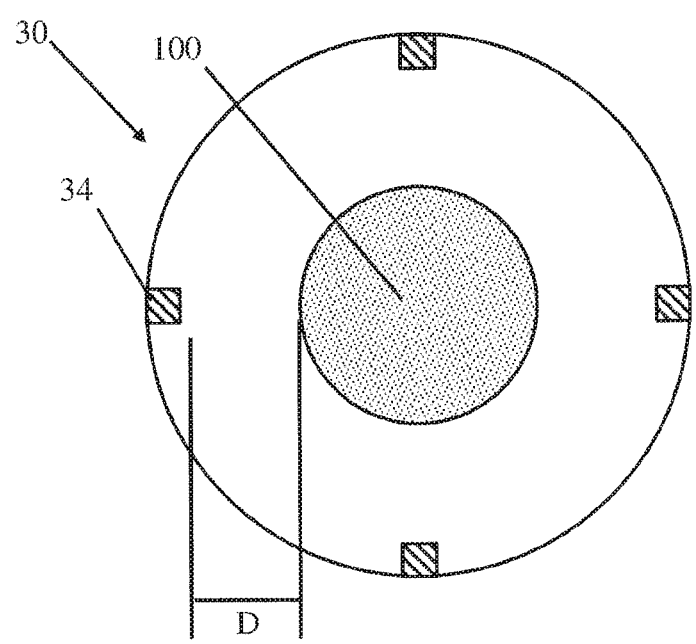
FIG. 5 is a schematic representation of a medical detecting system including one or more detectors that are spaced from an associated body portion.

In some embodiments, it may be desirable to reduce variability in readings from a source, such as a signal emitted from within a particular body portion, due to changes in small distances relative to a portion of a body being monitored. For example, variations in positioning of the detectors relative to a subject's ankle due to orientation and/or tightness of an associated ankle bracelet as well as changes in distance relative to a subject's skull due to different amounts of hair may result in variations in the detected signals. Without wishing to be bound by theory, this may be due to variations in the distance of the detectors relative to the body portion. To help minimize the percent difference in distance of a detector from an associated body portion between subjects, in one embodiment, the detectors may be maintained at a distance relative to a surface of the associated body portion which may help to provide consistent readings between different subjects. For example, as shown in FIG. 5, one or more detectors 34 may be maintained at a distance D relative to a surface of the body portion 100. In one such embodiment, the one or more detectors may be incorporated into an ankle bracelet 30 shown in the figures. Of course, embodiments in which the detectors are maintained at a distance relative to a body portion other than an ankle including the other various body portions described herein are also contemplated as the disclosure is not so limited.

Figure 6A:
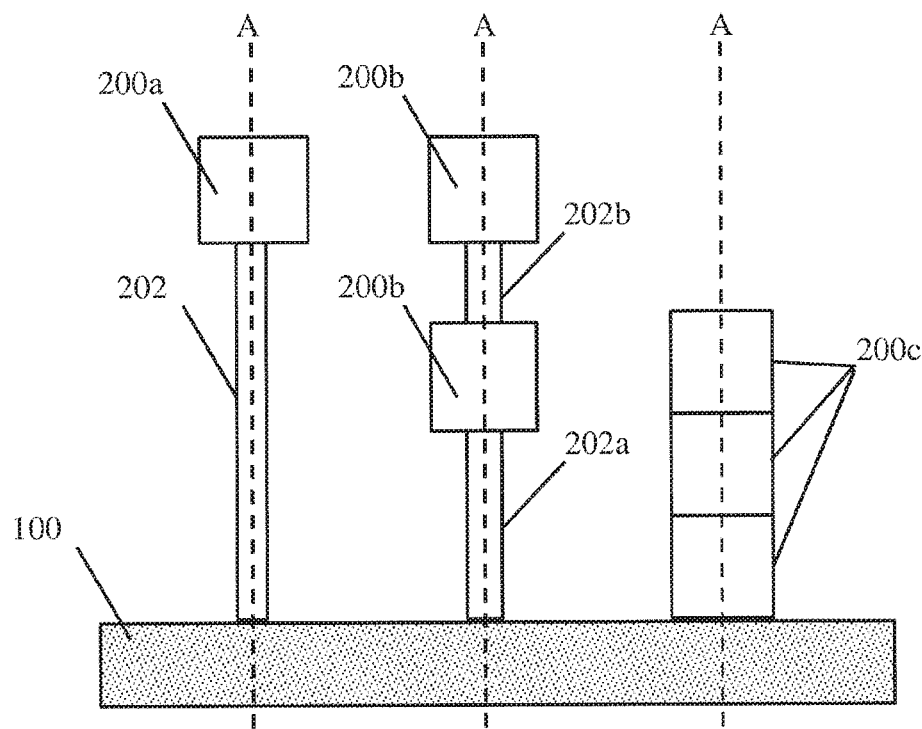
FIG. 6A is a schematic representation of different ways in which detectors may be arranged relative to the surface of a body portion.

FIG. 6A depicts several different ways in which one or more detectors may be maintained relative to the surface of a body portion 100. In one embodiment, one or more detectors 200 may be spaced from the surface of the body portion via a spacer 202. In the depicted embodiment, the spacer extends from a bottom surface of the detector towards the body portion when the medical device is in the worn configuration. Thus, the spacers may be located between the detector and the body portion. In another embodiment, a plurality of detectors 200b may be maintained in a spaced configuration relative to the surface of the body portion 100, and each other, by a first spacer 202a disposed between a lower surface of a first detector 202b and the body portion when in the worn configuration and a second spacer located between the first and second detectors. Consequently, the detectors may be maintained at first and second distances relative to the surface of the body portion. In yet another embodiment, a plurality of detectors 200c may be stacked on each other. Again, in such a configuration, the bottommost detector may be located at a first distance relative to the surface of a body portion and the detectors stacked on top of the bottommost detector would be located at subsequently increasing distances from the surface of the body portion. Of course, while the stacked detectors have been depicted as being disposed directly on the surface of the body portion, a spacer may also be located between the bottommost detector and the body portion as previously described.

It should be understood that any number of appropriate structures may be used to form the spacers in the above noted embodiments. For example, a solid footing made from a material that is substantially transparent to the radiation signals emitted from the associated body portion may be aligned with the detectors In such an embodiment, the spacer may extend from a lower surface of a detector towards the body portion, or another detector. However, embodiments in which the spacer is offset from the detectors and/or made from a radiopaque material are also contemplated. In yet another embodiment, a hollow cylinder, tapered cone, or any other appropriate shape may extend around a radiation sensitive portion of the detector and outwards from the detector towards the body portion when in the worn state. In such an embodiment, the spacer may be made of a radiopaque material to help shield the detector from extraneous signals from other sources and/or body portions. However, embodiments in which these spacers are made from a radiotransparent material are also contemplated. In view of the above, it should be understood, that a detector may be spaced from the surface of a body portion in any number of ways, and that spacers may be made from any appropriate material including, but are not limited to plastics, ceramics, and metals as the disclosure is not so limited.

In addition to the above, in some embodiments, it may be desirable for one or more spacers of a medical detecting system to have surfaces oriented towards a body portion that have curvatures that complement a corresponding curvature of the associated body portion. For example, a spacer may have a lower surface oriented toward a subject's body that has a concave curvature across the lower surface that complements the convex curvature of the underlying body portion. A corresponding flat surface, or any other appropriately shaped surface, may be formed on the opposing side of the spacer opposite the lower surface of the spacer. This opposing surface, and/or any other appropriate surface, may be used for attachment to a wearable structure and/or detector. In one such embodiment, one or more spacers are used to space one or more detectors from a head of a subject. Accordingly, the spacers may have lower surfaces oriented toward the subject's head that are curved to complement a curvature of the subject's head they are disposed and/or pressed against. Of course it should be understood that spacers associated with different body portions other than a head may also include surfaces that complement a shape of the underlying body portion and that these surfaces may include shapes other than a concave shape as the disclosure is not so limited.

Figure 6B:
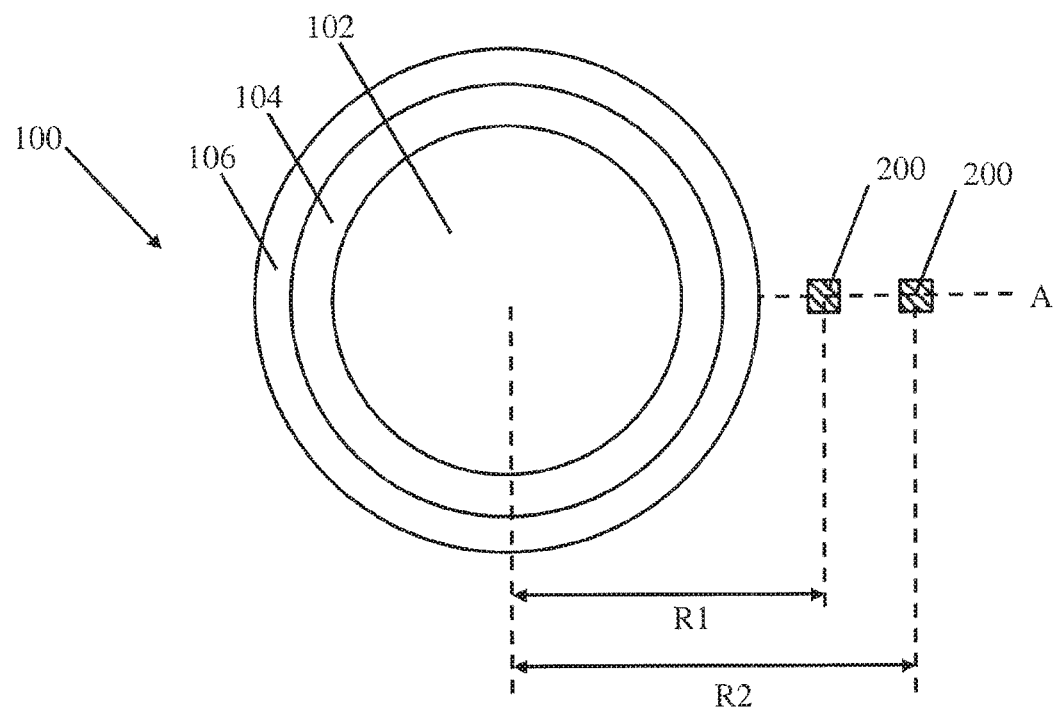
FIG. 6B is a schematic representation of detectors located at different radial positions relative to a body portion.

In embodiments where two or more detectors are located at different distances and/or radial positions relative to a body portion, in some instances, it may be desirable for the detectors to be arranged such that the detectors 200b and 200c, and their primary directions of sensitivity are aligned along an axis A and oriented towards a body portion of interest 100 as illustrated in FIGS. 6A-6B. Without wishing to be bound by theory, this may help reduce the complexity when deconvolving detected signal contributions from different portions of a subject's body at a particular location. However, embodiments in which the detectors and/or the corresponding primary directions of sensitivity of the detectors are not aligned along an axis (i.e. the detectors are laterally offset from one another relative to the body portion) and/or are not oriented towards the same body portion of interest are also contemplated as the disclosure is not so limited.

Some labeled compounds exhibit nonspecific binding in the skin, fat, and/or capillaries associated with a particular body portion. Further, sensitivity to this signal may be amplified when detectors are placed close to this region. In the following embodiments, methods and arrangements of detectors are described for distinguishing between specific activity versus non-specific activity of a labeled compound within a body portion of interest. Therefore, while the embodiments are described primarily with regards to the skin surrounding a head of a subject for the sake of clarity, it should be understood that the described methods and devices may be used with any organ or other body portion that may be associated with nonspecific dermal and/or subdermal signals.

As noted above, a detector arranged to sense a signal emitted from within body portion of a subject, such as a head, may detect a signal emitted from both the head interior (i.e. the brain) and the surrounding skin of the subject. To help differentiate these different signals, in one embodiment, a medical detecting system may include two or more detectors that are maintained at different distances relative to the surface of the subject's head or other appropriate body portion. Without wishing to be bound by theory, assuming that a signal sensed by a detector is emitted from the skin and a sphere of activity below it, it is possible to estimate the activity associated with the brain, or other interior body structure. Specifically for an assumed form of the radiation fields from the skin $C1*S(x)$ and from the Brain $C2*B(x)$, where C1 and C2 are constants that depend on the amount of activity, and S and B are the assumed form of the radiation fields at each position x relative to the skin and brain respectively, the combined system of equations can often be solved by an associated computing device, such as the noted controllers and/or remote computing devices, using 2 measurements at different points x which may then be used to calculate the radiation signal associated with the body portion of interest for subsequent usage in diagnosis and/or treatment of a subject as detailed further below. Because of the radial nature of the radiation fields S and B, in some embodiments it may be desirable for the detectors to be located at different radial positions to help resolve the difference between C1 and C2. FIG. 6B depicts one exemplary embodiment of a system that may be used to distinguish these different signal contributions from one another using two or more detectors 200 located at different radial positions R1 and R2 relative to the brain 102, skull 104, and surrounding skin 106 of the subject. Similar to the above, in some embodiments, the detectors 200 may be arranged such that the detectors, and their primary directions of sensitivity, are aligned along an axis A oriented towards the head of the subject.

Other ways to help distinguish between, and/or minimize, the uncertainties associated with detecting signals emitted from the skin versus the body portion of interest of a subject are also possible. For example, in one embodiment, one or more detectors may be displaced relative to the surface of a body portion as previously described. Without wishing to be bound by theory, since detectors placed directly against the skin of a subject show a much larger skin signal, moving the detectors away from the skin may help to greatly reduce the detected skin signal relative to the signal detected from the body portion of interest. An additional advantage is that for fixed uncertainty in the distance (e.g +/−1 cm) from the desired body portion, such as the brain, the uncertainty in the inferred signal is reduced as the overall distance is increased (i.e. the relative error in distance is smaller with increasing total distance). Of course, this increased distance also decreases the overall detected signal, e.g. the detected counts, from the associate body portion as well. To help counteract this effect, more sensitive detectors, longer count times, or any other appropriate method may be used as the disclosure is not so limited. Additionally, in some instances, a medical practitioner may inject a solution (e.g. saline or other appropriate solution), that does not contain a labeled compound, into an area underlying a detector. Without wishing to be bound by theory, this may help displace and/or remove labeled compound located in the skin underlying a detector which may also help to reduce a detected skin signal.

For embodiments where it may be desirable to reduce a skin signal, and/or where it may be desirable to reduce a variation in the distance from a body portion, a medical detecting system may include one or more detectors that are distanced relative to the surface of a body portion of the subject, including the head of a subject, by a distance that is greater than or equal to 1 cm, 2 cm, 3 cm, 4 cm, 5 cm, or any other appropriate distance. The detectors may also be maintained at distances less than or equal to 15 cm, 10 cm, 5 cm, or any other appropriate distance relative to a surface of the body portion. Combinations of the above ranges are also contemplated including, but not limited to, detectors located at distances between or equal to 1 cm and 15 cm, 5 cm and 15 cm, or any other appropriate combination of distances relative to a surface of a body portion. In addition to the above, distances both greater than and less than those noted above are also contemplated as the disclosure is not so limited.

Detectors may also be maintained at distances relative to one another as previously discussed as well. For example, in one embodiment, a difference in radial position between one or more detectors relative to a body portion when the system is worn may be greater than or equal to 0.5 cm, 1 cm, 2 cm, 3 cm, or any other appropriate distance. The difference in radial position may also be less than or equal to 15 cm, 10 cm, 9 cm, 8 cm, 7 cm, 6 cm, 5 cm, 4 cm, 3 cm, or any other appropriate distance relative to a surface of the body portion. Combinations of the above ranges are also contemplated including, but not limited to, detectors with differences in their radial positions between or equal to 1 cm and 5 cm, 0.5 cm and 15 cm, or any other appropriate combination of distances relative to a surface of a body portion. In addition to the above, distances both greater than and less than those noted above are also contemplated as the disclosure is not so limited.

In another embodiment, a skin signal associated with a body portion, such as the head, may be minimized by reducing a flow of blood to the skin associated with the portions of the head being imaged. This may be accomplished in a variety of ways including both compression of the skin, compression under the skin (e.g. injection of a solution under the skin), by cooling, moving a portion of a subject's body (e.g. moving a subject's arm up and down relative to their head), and/or using any other appropriate method to reduce blood flow to the skin associated with a body portion of interest as detailed further below.

Figure 7:
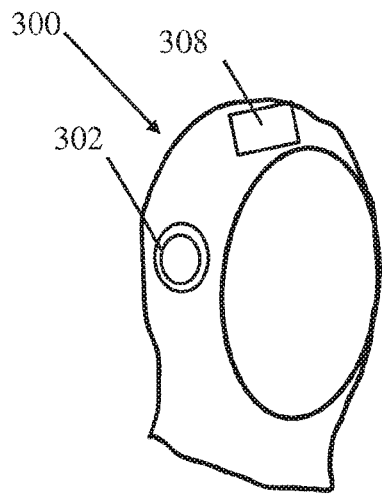
FIG. 7 is a schematic perspective view of a medical detecting system including a compressive cap and/or cooler.
Figure 8:
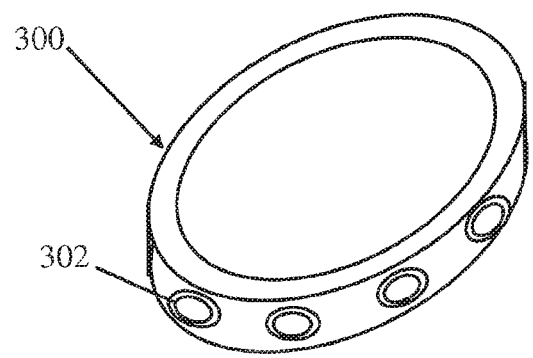
FIG. 8 is a schematic perspective view of a medical detecting system including a compressive band.

In some embodiments, a wearable structure may include one or more compressive features that restrict blood flow to a subject's skin proximate to an associated location of one or more detectors when a system is worn on a subject. Depending on the particular embodiment, these compressive features may either be fixed in position on the wearable structure, or they may be repositionable on the wearable structure. Additionally, in some embodiments, the compressive features may apply a compressive pressure at locations removed from the associated positions of the detectors and/or at locations surrounding the detectors. For example, as shown in FIGS. 7 and 8, a wearable structure 300 may be worn on the desired body portion. In such an embodiment, at least a portion of the structure applies a compressive pressure to the body portion it is worn over that may restrict the blood vessels within the associated skin of the subject thus restricting a flow of blood to the body portion. In some applications , the wearable structure may apply a compressive force to the entire body portion it is disposed on, such as in the case of a cap or hood worn over the entire head, and as shown in FIG. 7. Alternatively, a wearable structure may apply pressures to only a portion of the associated body portion similar to the band of FIG. 8. Depending on the embodiment, the compressive pressures may be applied using an elastic band or tightening mechanism integrated into a wearable structure that applies pressures around the body portion of interest, such as the subjects head, to restrict blood flow to the skin located above, i.e. downstream within the capillary and arterial network, the locations where the pressure is applied to the skin. In another embodiment, an inflatable cuff may be used to apply the desired compressive force.

In the above embodiments, the wearable structures may be made out of any appropriate material and/or configuration that is capable of applying a compressive force to the skin of a subject's head to restrict blood flow to skin associated with one or more detectors. Appropriate materials include elastic materials or fabrics; relatively non-stretchable but flexible fabrics, webs, or non-woven materials associated with a tightening mechanism such as laces, buckles, zippers, elastic regions, and other appropriate mechanisms; and/or any other structure capable of applying a compressive force to the skin of a subject's head.

In addition to embodiments where a wearable structure itself directly applies a compressive force to an associated body portion, in some embodiments, a wearable structure 300 may include one or more protrusions 304 that are pressed against the skin of the associated body portion to restrict a flow of blood to the skin located within the region the protrusion is pressed against and/or downstream from the protrusions, see FIGS. 7-8. Further, the protrusions may form a single continuous surface that is pressed against the subject's skin and/or they may form closed loops of any shape that may be pressed against the surface of a body portion. Appropriate shapes include, but are not limited to: a circle; square; triangle; rectangle; oval; a torus, a ridge forming a closed loop extending around the entire body portion or a sub portion of the body portion; or any other desirable shape. While protrusions formed on a wearable structure are described above, it should be understood that the described protrusions, and similar features, may be integral or separate from a wearable structure as the disclosure is not so limited. Further, in some embodiments, the features either formed on, or otherwise associated with, a wearable structure may be substantially rigid. These features forming a protrusion may also take any number of other forms including, for example, an inflatable structure, such as an integral inflatable bladder, or other integral spacer, used to compress the underlying skin and/or lift a detector relative to an adjacent body portion. In either case, similar to the above embodiments, the protrusions associated with a wearable structure may be biased towards the surface of a body portion using any appropriate method including elastic materials or fabrics; relatively non-stretchable but flexible fabrics, webs, or non-woven materials associated with a tightening mechanism such as laces, buckles, zippers, elastic regions, springs, and/or other appropriate mechanisms or structure capable of applying a compressive force to press the protrusions against the surface of a body portion without interfering with a desired signal being detected.

In addition to the above, in some embodiments, protrusions that are pressed against the surface of a body portion may extend around and/or cover a field of view of one or more associated detectors. Thus, when pressed against the surface of a body portion, the described protrusions may reduce a flow of blood to the skin located within and/or beneath the area the protrusions are pressed against. Due to the detector's having field of views that are collocated with this area, and/or downstream from these protrusions within a capillary or arterial network of the skin, a skin signal sensed by the detectors may be reduced.

Figure 9A:
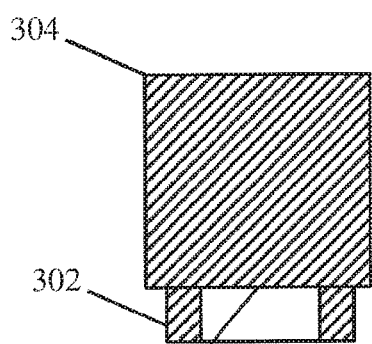
FIG. 9A is a schematic cross-sectional view of a radiation detector including a protrusion for applying a compressive force to skin positioned adjacent to the detector.
Figure 9B:
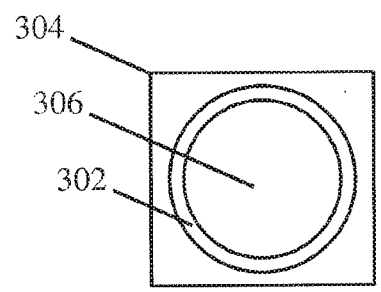
FIG. 9B is a schematic bottom view of the radiation detector of FIG. 9A.

The above described protrusions may be made from any appropriate material including plastics, metals, elastomers, ceramics, or any other material that is sufficiently rigid to apply a pressure to the skin it is pressed against. Depending on the embodiment, the protrusions may be located within a wearable structure, or they may be disposed on an inner surface of the wearable structure such that they are pressed against the skin of a subject. In instances where the protrusions extend over the sensitive region of a detector (i.e. are located within a field of view of the detectors), the protrusions may be made from a material that is substantially transparent to the radiation signals emitted from the associated body portion. In another embodiment, and as shown in FIGS. 9A-9B, a protrusion 302 may be integrated with a detector 304 such that the protrusion forms a closed loop extending outwards from a lower surface of the detector towards the skin, or surface, of a body portion of interest when in the worn condition. As illustrated in the figure, the protrusion may extend around an area 306 of the detector corresponding to a detection aperture and/or a portion of the detector sensitive to the desired radiation signal. Thus, in such an embodiment, the protrusion would not cover a field of view of the detector and may be made from a radiopaque material if desired.

While the use of separate compressive features are described above, in some embodiments, a spacer used to distance a detector from a body portion may also be used to apply a compressive force to the skin of a body portion underlying the spacer. Again, this may help to reduce an observed skin signal from the associated body portion due to the applied compressive force. However, as detailed above, embodiments in which a spacer does not apply a compressive force are also contemplated. Additionally, in some embodiments, a combination of spacers and separate compressive features may be used as the disclosure is not so limited.

It should be understood that any appropriate pressure may be applied by a wearable structure, and/or protrusion associated with the wearable structure, to the surface of a body portion when in the worn state. However, in one embodiment, a pressure applied to the skin of a body portion may be greater than a peak blood pressure (i.e. systolic pressure) of a subject in a particular body portion. In one specific embodiment, a pressure applied by a wearable structure and/or associated protrusion to the skin of an underlying body portion may be greater than or equal to 200 mm Hg, 300 mm Hg, 500 mm Hg, 600 mm Hg, or any other appropriate pressure. Correspondingly, a pressure applied by the wearable structure and/or protrusion to the skin of an underlying body portion may be less than or equal to 1000 mm Hg, 800 mm Hg, 600 mm Hg, 500 mm Hg, or any other appropriate pressure. Combinations of the above ranges are contemplated including, for example, between or equal to 200 mm Hg and 1000 mm Hg, 500 mm Hg and 1000 mm Hg, or any other appropriate combination. Of course pressures both greater than and less than those noted above may be used as the disclosure is not so limited.

While the above noted pressures applied by a wearable structure, and/or protrusions associated with the wearable structure, may be applied in any desirable location to restrict a flow of blood towards one or more locations on a subject's skin associated with one or more detectors, including skin located on the head, in one embodiment, one or more of the above noted features may be used to apply a ring of pressure around the ear of a subject which may help to block some of the principal arteries feeding the skin in this region. Further, a detector may be collocated with this region for detecting radiation emitted from a subject's head at this location.

In yet another embodiment, a flow of blood to the skin of a body portion, such as a subject's head, may be reduced by cooling the skin. Cooling of the skin and other subdermal tissues may be accomplished in any number of ways. For example, as shown in FIG. 7, in one embodiment, a cooler 308 may be integrated with a portion of the wearable structure, or may be applied separately to a subject's head, such that it cools the subject's skin in one or more locations. Appropriate types of coolers include, but are not limited to: a cold thermal mass (e.g. ice pack) in thermal contact with the subject's skin; a heat exchanger in thermal contact with the subject's skin where a flow of cool fluid flows through the heat exchanger; an endothermic chemical reaction (e.g. solid ammonium nitrate or urea dissolving in water) contained within a compartment in thermal contact with the subject's skin; thermoelectric cooling using a Peltier cooler; a blower pump, fan, or turbine that flows cool gas or fluid onto or over the subject's skin; and/or any other appropriate configuration capable of cooling the skin of a subject. Additionally, depending on the particular embodiment, cooling may either be applied to a portion of a body portion proximate one or more associated detectors, to a location removed from the detectors, to an entire surface of the body portion, and/or other appropriate body portion of the subject.

Depending on the particular embodiment, a cooler may cool the skin of an associated body portion by any appropriate temperature change. However, in one embodiment, a cooler may cool the surface of a body portion by greater than or equal to 1° C., 5° C., 10° C., or any other appropriate temperature. Correspondingly, the cooler may cool the surface of the body portion by less than or equal to 20° C., 10° C., and/or any other appropriate temperature. Combinations of the above ranges are contemplated including a temperature change of the surface of the body portion between or equal to 1° C. and 20° C. However, other combinations of the above ranges as well as temperature changes both greater than and less than those noted above are also contemplated as the disclosure is not so limited. Additionally, in some instances, a subject, and/or a portion of a subject's body, may simply be placed in a cooler environment such as a room with a lower ambient temperature, an ice bath, or other appropriate environment capable of providing the desired cooling.

In some instances, such as when detectors located far from away from the head of a subject are used, shielding of the detector may be desirable to reduce, and/or eliminate, signals detected from unwanted sources such as the liver or other portions of the body. Depending on the particular embodiment, the shielding may either be integrated with the individual detectors and/or shielding may be placed on a chair, table, bed, and/or integrated into a wearable garment to locate the shielding between the unwanted radiation source and the detectors. For example, a leaded vest might be worn on a subject's torso to reduce a detected signal from the liver when measuring signals emitted from the subject's head.

Figure 10:
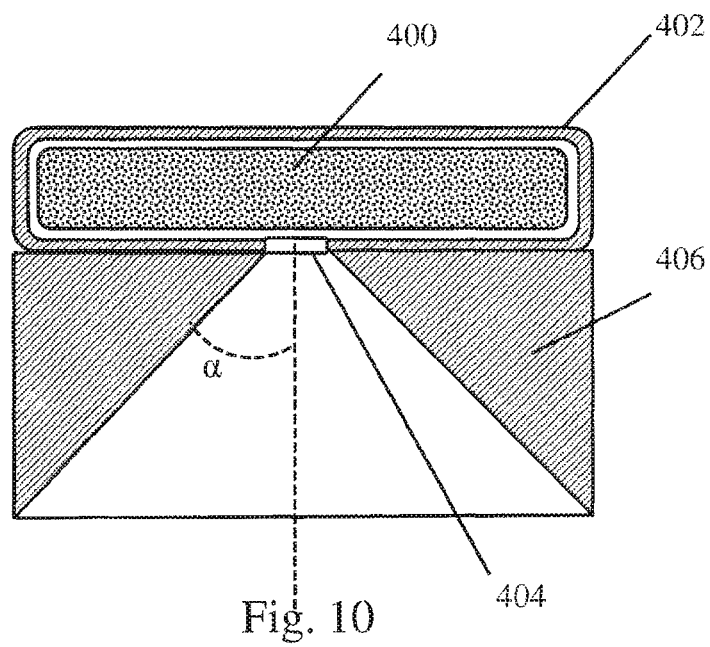
FIG. 10 is a schematic cross-sectional view of a radiation detector including shielding.

FIG. 10 depicts an embodiment of a detector including shielding. In the depicted embodiment, the detector 400 is surrounded on one or more sides, and in some embodiments on all sides, by a radiopaque housing 402. The housing includes an aperture 404 aligned with an active detection region of the detector. Thus, the housing shields the detector from signals originating from different directions while permitting signals to pass through the aperture where they are detected by the detector. In addition to shielding the detector, in some embodiments, it may be desirable to further limit the angle of acceptance for a detector when used for some applications. This may be of particular benefit in applications such as limiting the area of detection to a specific location or structure and/or when performing computed tomography. In such an embodiment, a collimator 406 made from a radiopaque material may be integrally formed with, or otherwise attached, to the housing of the detector. Alternatively, the collimator may be indirectly associated with a detector as the disclosure is not so limited. Regardless, in the depicted embodiment, the collimator may limit an angle of acceptance a of the detector. While a generic collimator has been depicted, any number of types of collimators may be used depending on the type of emission being detected. Appropriate collimators for use with radioactive tracers include, but are not limited to, parallel hole collimators, slant hole collimators, converging and diverging collimators, fan beam collimators, as well as pin hole collimators such as the cone shaped arrangement depicted in the figure. Depending on the application, a collimator may restrict the angle of acceptance of a detector to an angle a that is less than or equal to 60°, 45°, 30°, and/or 15°. However, angles both larger and smaller than those noted above are also contemplated.

In some instances, it may be desirable to perform computed tomography, and in some applications specifically Positron Emission Tomography (PET), using the detectors described herein. In such an embodiment, two or more detectors associated with a wearable structure may form one or more pairs of detectors located on opposing sides of a body portion of interest when in the worn condition. Further, in some embodiments, the detectors and associated controllers may record the time of impact of each incident gamma ray so that coincident detection (PET) may be enabled.

Figure 11:
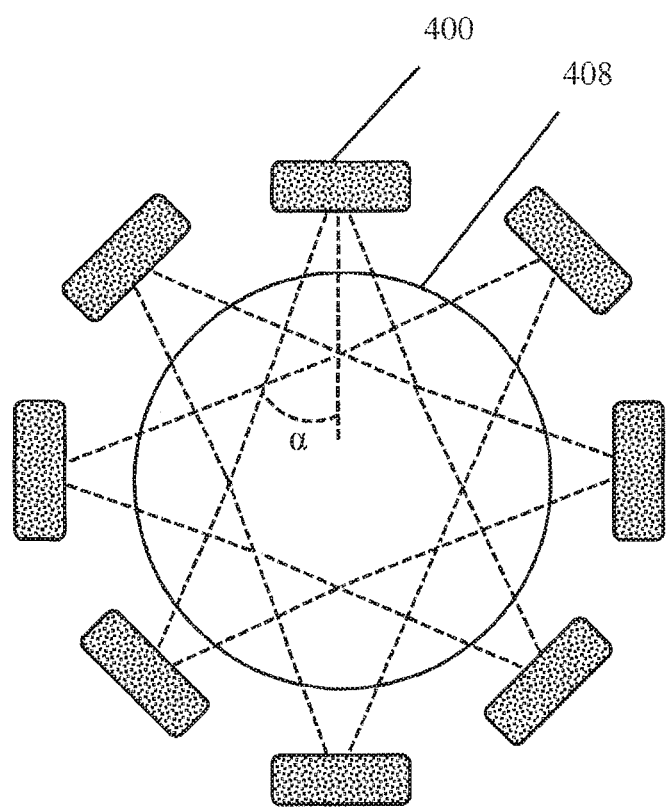
FIG. 11 is a schematic representation of a plurality of radiation detectors arranged around the periphery of a body portion for performing computed tomography imaging.

FIG. 11 depicts one embodiment of a plurality of detectors 106 including an angle of acceptance a for use in computed tomography. As depicted in the figure, the detectors are arranged around the exterior of a body portion 112. The body portion may correspond to any appropriate body portion, including, but not limited to a head, arm, torso, or leg of a subject. Further, the detectors may be attached to a wearable structure worn on the body portion, not depicted, for maintaining the detectors proximate to the body portion. In addition to the above, the detectors are positioned so that they have overlapping fields of view as illustrated by the acceptance angles depicted in the figure. This arrangement of detectors facilitate detecting and locating the source of emissions, such as radiation, emitted by a tracer located within the body portion. Specifically, the signals detected by the individual detectors are output to a computing device using any appropriate method and are then used to form a computed tomography image or signal intensity mapped onto the body portion which may then be used to evaluate the presence, concentration, and/or changes over time of a tracer within a sub part of the body portion being monitored. For example, detectors arranged around the head of a subject may have angles of acceptance directed towards a portion of the brain that is of interest for a particular diagnostic or therapeutic procedure. In such an arrangement, the detectors may be used to perform real time imaging of the desired body portion and/or signal detection for diagnostic and/or therapeutic purposes.

Figure 12A:
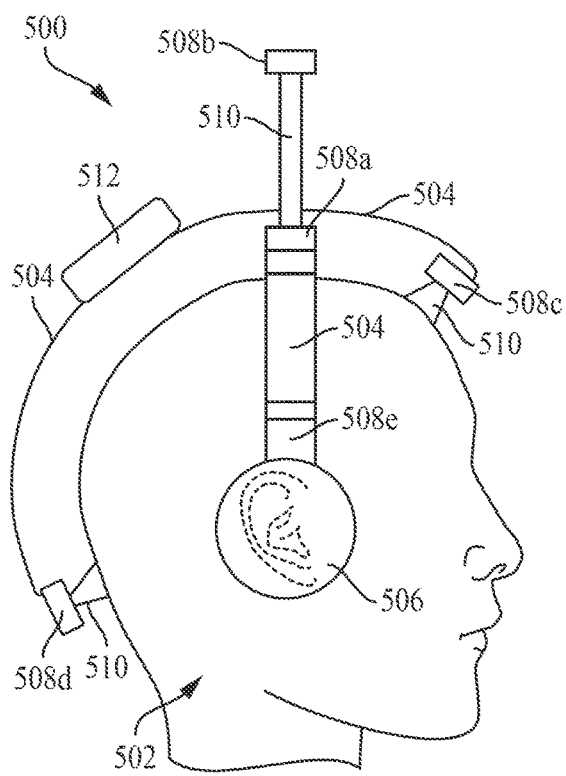
FIG. 12A is a schematic side view of a medical detecting system worn by a subject.
Figure 12B:
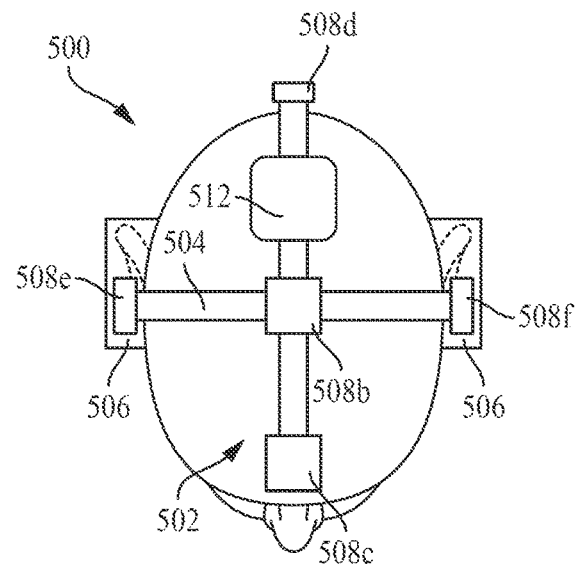
FIG. 12B is a schematic top view of the medical detecting system of FIG. 12A.
Figure 12C:
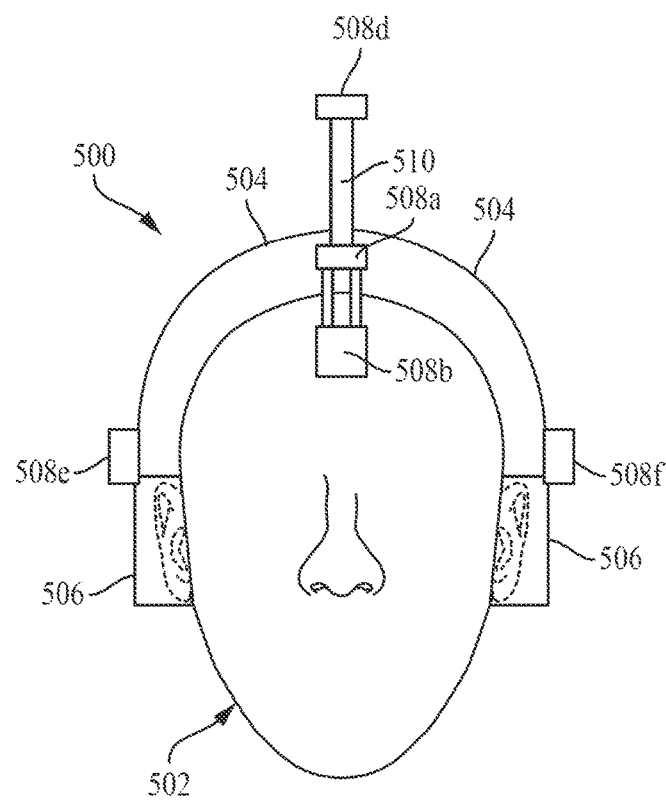
FIG. 12C is a schematic front view of the medical detecting system of FIG. 12A.

FIGS. 12A-12C show various views of one embodiment of a wearable medical detecting system. In the depicted embodiment, a medical detecting system 500 is worn on a subject's head 510. The wearable detector system includes a wearable structure made from one or more flexible curved arms 504 that may include one or more detectors that are either permanently, and/or adjustably, positioned along a length of the flexible arms. The flexible curved arms extend around the subject's head and may be made from a sufficiently elastic material such that when worn on the subject's head, the flexible arms apply a steady pressure to retain the wearable structure on the subject's head. Depending on the particular embodiment, the flexible arms may be integrated with any number of different other features to form a wearable structure. For example, the flexible arms may be integrated with, and/or attached to, a single headphone, or a pair of headphones, 506 that are positioned to be worn over a subject's ears. The headphones may be used to play soothing music, communicate a message that the subject finds soothing and orienting, and/or to communicate instructions. Other structures that the flexible arms may be integrated with include, but are not limited to, a hat, helmet, chin strap, vest, shirt, cap, shoe, glove, bracelet, sleeve, legging, sock, stocking, collar, head band, arm band, leg band, waist band, shorts, pants, body sleeve, corset, eyeglasses, headphone, exoskeleton, frame, and/or any other appropriate structure capable of wearing on a body portion of a subject.

In addition to the one or more flexible arms, a medical detecting system depicted in figures may also include a plurality of detectors disposed along the lengths of the different flexible arms and distributed around a subject's head 502 to monitor signals emitted from different portions of the subject's brain. In the depicted embodiment, the system includes a first detector 508a attached to a central portion of the detector system located at a top portion of the subject's head when worn. A second detector 508b is spaced vertically upwards from the first detector when worn on the head such that the first and second detectors are located at first and second radial positions relative to the subject's head as previously described. Additional detectors 508c-508d are located on a frontal upper lobe of the subjects had and a substantially opposing lower rear lobe of the subject's head. Of course, while specific detector locations have been described above, and illustrated in the figures, other detector locations relative to a subject's head may also be used as the disclosure is not so limited. Additionally, any number of detectors both greater than and less than those noted in the depicted embodiment may also be used.

The above noted detectors may be attached to an associated wearable structure in any appropriate fashion. For example, in one embodiment, the detectors and/or associated spacers are permanently attached to the wearable structure using any appropriate attachment method. However, in some embodiments a detector and/or one or more associated spacers may be selectively attachable to different portions of a wearable structure using appropriate selective attachment methods including but not limited to snap connectors, buttons, touch fasteners, clips, magnets, interlocking mechanical features, threaded fasteners, and/or any other applicable method. Additionally, in some embodiments, the detectors and/or spacers may simply be attachable to each other to facilitate stacking of the detectors and/or spacers. For example, the detectors and/or spacers may be selectively attachable to one another using snap connectors, buttons, touch fasteners, clips, magnets, interlocking mechanical features, threaded fasteners, and/or any other applicable method. Alternatively, one or more brackets attached to the wearable structure may be shaped and sized to accept and retain a plurality of detectors therein in a stacked configuration relative to a body portion of interest.

In addition to the above, it may be advantageous to place detectors in locations along a body portion that show enhanced signal to noise ratio. For example, certain positions on a subject's head have higher uptake in the region above the skull, and certain positions exhibit stronger brain signals. Based on the ratio of these signals, one or more detectors may be located at positions exhibiting a reduced noise to signal ratio. For example, one or more detectors may be positioned to detect signals emitted from a region of a body portion associated with a target anatomy and/or disease. Additionally, in some embodiments, these regions may also exhibit a reduced skin signals. For instance, a region on the side of a subject's head located above the ear ranging from the temple towards a rear of the head to a similar angle behind the ear may exhibit a higher brain to non-brain signal than other regions on the surface of the head which may be useful in certain applications such as beta amyloid detection. In one embodiment, these locations may correspond to one or more radiation detectors centered at Cz or Pz in a 10-20 EEG layout. Additionally, another location exhibiting a reduced noise to signal ratio is located at a top portion of a subject's head at a distance between 1 cm and 10 cm from a top of the head. Based on the forgoing, and as shown in FIGS. 12A-12C, detectors 508e and 508f may be positioned on opposing sides of the subject's head above the ears at a position between a temple and a rear of the head when in the worn position. In one embodiment, these locations may correspond to one or more radiation detectors disposed within a region including F3, C3, and P3 and/or F4, C4, and P4 in a 10-20 EEG layout. While single detectors have been depicted above the ears on either side of the head, it should be understood that a plurality of detectors may be located in this region which may be advantageous for certain sensing applications. Additionally, the first and second detectors 508a and 508b may be maintained between 1 cm and 10 cm from the top of a subject's head when worn.

In addition to the above, to help reduce noise associated with a detected signal, a medical detecting system may include one or more noise channels. These noise channels may correspond to a shielded detector disposed on the wearable structure in electrical communication with a controller of the system and that is isolated from the radiation signals been detected by the other detectors (i.e. the detector is shielded). This may help with various types of noise sources including vibrations which may set off certain types of detectors including scintillator based and pin diode type detectors. In such an embodiment, a noise channel may detect signals with energies that are lower than those expected for a desired radiation signals such as that from a gamma ray and output the detected noise signal to the controller. Correspondingly, the controller of the medical detecting system may use this noise signal to determine that some fraction of the signal hits are to vibration, or other noise source, and may be disregarded when analyzing the detected signals.

Depending on the embodiment, a medical detecting system may also include detectors arranged to sense a signal emitted from one or more lymph nodes that the brain clears to when worn by a subject. This may be of benefit in a number of applications including, but not limited to, sensing an amyloid burden in the brain by detecting higher specific binding which be evidenced by lower clearance rates of a tracer to the associated lymph nodes.

As shown in FIGS. 12A-12C, one or more controllers 512 may also be attached to one or more of the flexible arms, or any other appropriate portion of a wearable structure. The one or more controllers may be in electrical communication with the detectors 508a-508f of the medical detector device for controlling the system and/or receiving signals from the detectors as previously described. The controller may also have one or more LEDs, displays, or other indicators that may be used to communicate a state of the one or more detectors using different modes of operation (on/off, different colors, etc.) to indicate if a particular detector is functioning properly and/or display information related to the distribution of the radiation field.

Similar to the previously described embodiments, the embodiment depicted in FIGS. 12A-12C uses a plurality of spacers 510 to maintain the detectors 508a-508f spaced from the surface (i.e. skin) of the subject's head by a desired distance. As discussed previously, this distance between the detectors and the subject's head may be maintained in any number of ways. However, in the depicted embodiment, the spacers extend inwards from the detectors and/or flexible arms such that the detectors contact the subject's head in the worn condition. The detectors are depicted as being in direct contact with the one or more spacers with a sensitive axis of the detectors aligned with a central axis of the spacers. However, in some embodiments, the spacers may be offset from the locations of the detectors such that they are not aligned with one another. Additionally, the detectors may either be in direct contact with the spacers or in indirect contact with the spacers through another feature such as one or more spacers distributed along a length of the flexible arm themselves as the disclosure is not so limited.

In the depicted embodiment, the detectors have been depicted as being located at a fixed distance along the lengths of the flexible arms. However, in some embodiments, it may be desirable to move the detector positions to appropriately locate them for a particular sensing application. For example, the one or more detectors may be located at fixed positions along a length of one or more flexible arms that are adjustable in length. Consequently, the arms may be adjusted to appropriately locate the detectors at a desired position. The arms may be adjustable in length using any appropriate mechanism including, but not limited to: telescoping arms; selectively removable segments; arms received in one or more slots or holes that may be selectively moved into and out of the slots or holes prior to being locked in place; or any other appropriate arrangement. Alternatively, the one or more detectors may be movable along a length of the associated flexible arms. This may be accomplished in a number of ways including for instance: a plurality of attachment points disposed along a length of the one or more flexible arms and a mating coupling disposed on the detector for selectively attaching the detector at a desired location along the length of the flexible arms. Appropriate methods for locking the detectors in place include, magnetic materials, snaps, interference fits, interlocking features, threaded fasteners, tongue and slot arrangements, and/or any other appropriate feature capable of selectively positioning one or more detectors in one or more desired locations along the length of the flexible arms.

In certain applications, it may be desirable for a medical detecting system to be movable between a wearable configuration and storage configuration appropriate for when the system is not in use. For example, in reference to the embodiments described in FIGS. 12A-12C, the one or more flexible arms of the device may be connected to a pivotable connection, such as a pin joint, at a central portion of the device. Thus, one or more of the flexible arms may be rotated between a wearable configuration and a storage configuration to collapse the device from a first larger sized to a second smaller size. Of course, other methods for moving the device between the configurations are also contemplated as the disclosure is not so limited. For example, telescoping flexible arms may be used to reduce the size of the system when not in use. Similarly, one or more joints along a length of the flexible arms may permit the arms to be at least partially folded in one direction while resisting movement in another opposing direction to permit the device to be worn in one configuration and stored in an at least partially collapsed configuration.

In some applications it may be desirable to calibrate and/or ensure a particular detector is functional during operation of a detector system. However, in contrast to when a large signal is detected, it may be difficult to distinguish between a zero signal and a non-operational detector. Consequently, in some embodiments, the functionality of a particular detector may be determined by using a low level radiation source that may either be permanently, or temporarily, located near a radiation sensitive portion of the one or more detectors. This low level signal, may then be used as an indication that the detector is functional when detected. Similarly, this same radiation source may be used to calibrate a detector due to the detected signal corresponding to a known radiation source with a known intensity. In instances where the radiation source is integrated with a detector, it may be desirable for the source to emit substantially less than an expected radiation signal emitted from a body portion of a subject containing a radioactive tracer to avoid an excessive noise to signal ratio. While any appropriate source may be used, it may be desirable for the source to be between or equal to 0.1 uCi and 10 uCi of $^{137}$Cs or other appropriate radiation source. Additionally, sources in amounts and/or emitting radiation intensities both greater and less than that noted above, as well as different forms of radiation, are also contemplated as the disclosure is not so limited.

Figure 13:
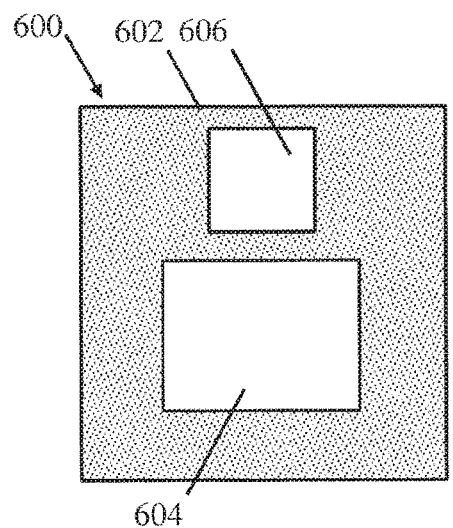
FIG. 13 is a schematic representation of a radiation detector including a radiation source.

FIG. 13 depicts one embodiment of a detector 600 that may be used to determine whether or not the one or more detectors of a medical detecting system are functional. As shown in the figure, the detector includes a housing 602. Depending on the particular embodiment, the housing may either be shielded, or unshielded, as the disclosure is not so limited. An active detecting component 604, such as those noted previously for detecting a radiation signal, may be disposed within any appropriate portion of the housing such that a strength of the source and a distance between the source and active detecting component are sufficient to permit the source to be detected by the active detecting component. As described above, a radioactive source 606 may be located proximate to the active detecting component within the housing. Consequently, the active detecting component may sense a radiation signal emitted from the source even in the absence of a radioactive signal emitted from an associated body portion that the detector is monitoring.

Figure 14:
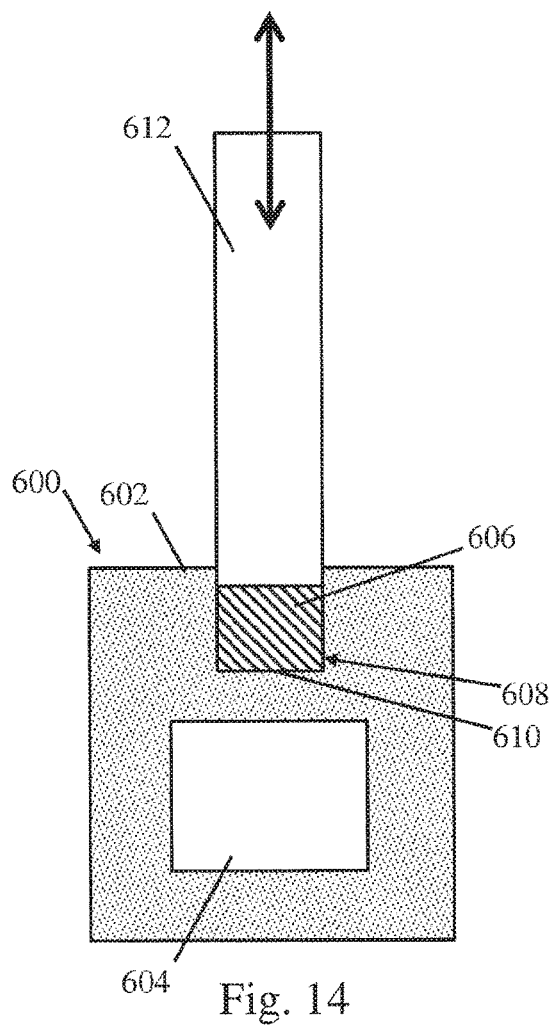
FIG. 14 is a schematic representation of a radiation detector and associated rod including a radioactive source on a tip inserted into the radiation detector.

FIG. 14 illustrates another embodiment of a detector using a radioactive source to determine whether or not a particular detector 600 is functioning. In the depicted embodiment, the detector again includes a housing 602 and an active detecting component 604 disposed therein. In this embodiment, the housing includes a cavity 608 that selectively receives a radioactive source 606 located on an end 610 of a rod 612, or other structure, that may be inserted into the cavity as indicated by the arrow in the figure. A strength of the source located on the rod end and a distance between the cavity and active detecting component may be sufficient to ensure that the source is detected when the rod is inserted into the cavity. Thus, a user, such as a medical practitioner, may insert the rod into the cavity either prior to, or during use, of the medical imaging device, to determine whether or not a signal is detected by the one or more detectors to ensure that the medical detecting system is functioning properly.

While the above described detector includes a cavity into which a rod is inserted, in some embodiments, the rod, or any other appropriately shaped object, may be placed within sufficient proximity to the detector to permit the active detecting component to sense a signal from a source associated with the rod or object. For example, an object including radioactive material may be placed proximate to a mark on a surface, a projection on a surface, or any other appropriate indicator of where to position a source to be sensed by the detector. Additionally, in instances where a cavity is used to help position the rod or object, the cavity may have any appropriate depth and/or shape including circular, square, rectangular, ovular, or any other appropriate configuration as the disclosure is not so limited.

In yet another embodiment, a medical detecting system including one or more detectors may including a docking or charging station that the system may be attached to or otherwise placed proximate to. The docking or charging station may include a radioactive source that is a known distance from the one or more detectors when the system is docked with the charging and/or docking station. The detectors may then detect a signal emitted from the radioactive source that is compared to an expected signal when the system is associated with the charging and/or docking station. A controller of the system may then compare this signal to an expected signal stored in memory to confirm the functionality of the one or more detectors. The controller may then operate an appropriate display or indicator to indicate an operational state of the system to a user.

Figure 15:
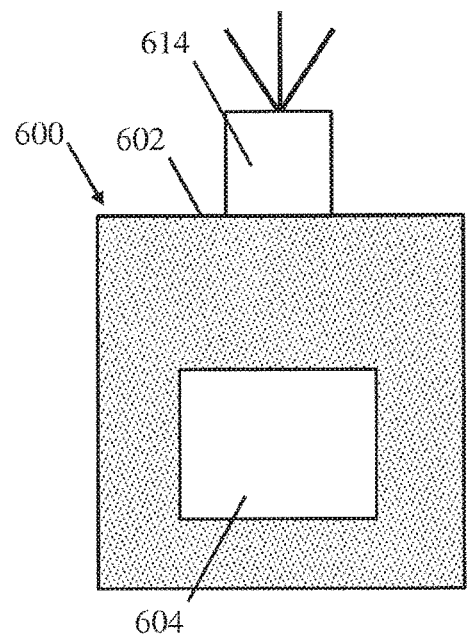
FIG. 15 is a schematic representation of a radiation detector including a light emitting diode.

FIG. 15 depicts an embodiment of a detector 600 including a housing 602 and an active detecting component 604 disposed therein. The detector may also include an indicator 614 disposed on any appropriate portion of the housing, such as one or more light emitting diodes (LEDs) disposed on the housing that may change color, turn on or off, change intensity, and/or alter its operation in any other appropriate fashion to indicate visually to a user and/or subject that the detector is functioning, and/or to communication any other relevant information to a user related to a detected signal. In one such embodiment, an indication of a functioning detector may either be based simply on power being delivered to the detector and/or may be based on a controller of the detector receiving a signal picked up by the detector as described previously, and the controller appropriately activating the indicator. In addition to indicating that the detector is functional, in some embodiments, the indicator may also change color, change intensity, and/or otherwise alter its operation in any other appropriate fashion to indicate different intensities of a detected signal. For instance, an indicator may include multiple LEDs, or other light sources, of different color that may be activated either individually and/or sequentially to indicate changes in intensity of a detected signal. Alternatively, in another embodiment, multiple LEDs or other light sources associated with the detector may be activated sequentially to indicate different detected signal thresholds. In yet another embodiment, an LED, and/or any other light source, may change an intensity of an emitted light to indicate differences in the strength of a detected signal. For example, an indicator may be activated or turn a particular color, e.g. from red to green, to indicate that a radiation signal has been detected. This indication may be based on a threshold signal determined using an expected background activity, detector sensitivity, and/or the radiation signals sensed by other detectors. Additionally, in another embodiment, when a detector is determined by a controller of a medical detecting system to be non-functional, the controller may indicate this condition to a user and/or subject by activating an appropriate indicator such as a red LED. Alternatively, other types of indicators including, for example, text, numerals, or other sight based outputs may be output on a display visible to a user and/or subject to communicate the desired information.

While several embodiments of an indicator capable of communicating an operational state of a detector and/or differences in the intensity of a detected signal have been described above, should be understood that any appropriate type of indicator may be used as the disclosure is not so limited. For example, an information may be communicated to a user and/or subject in any appropriate manner including using a display, an associated computing device, lights, LEDs, sound, bistable displays, or any other appropriate type of indicator.

In certain applications, it may be desirable to detect a radiation signal associated with a particular bolus of a labeled compound including a radioactive tracer either prior to, and/or just after administration of the labeled compound into a subject. For example, this detected signal may be used to normalize signals detected by other detectors of a medical detecting system and/or to estimate an amount of administered and/or residual dose of a known labeled compound.

Figure 16:
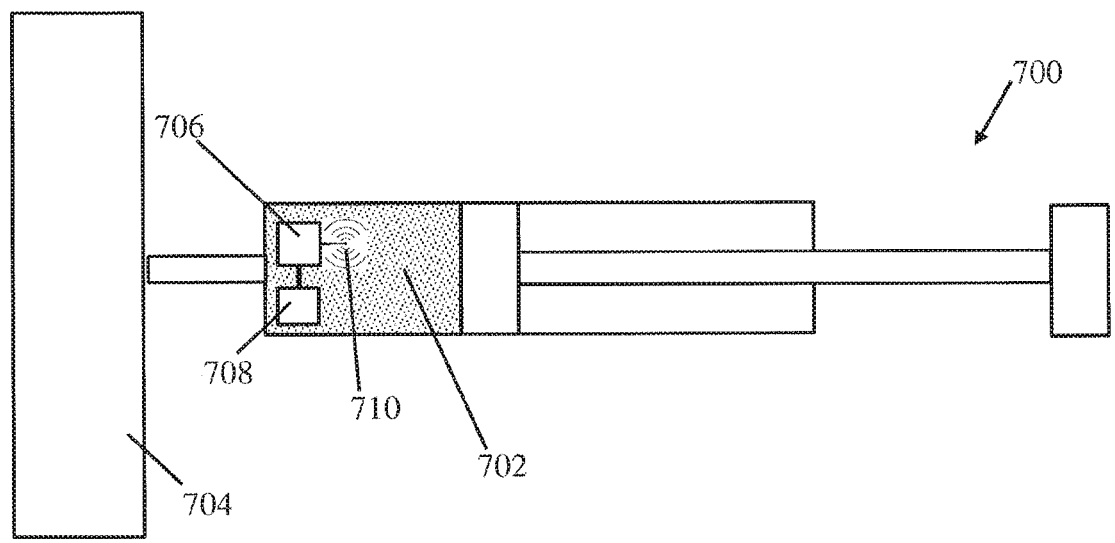
FIG. 16 is a schematic representation of a syringe including a radiation detector being used for administering a labeled compound labeled with a radioactive tracer into a subject.

FIG. 16 illustrates one possible embodiment of a device for sensing an initial radiation signal from a bolus of labeled compound. In the depicted embodiment, a syringe 700 includes a bolus 702 of labeled compound with a radioactive tracer 702. The bolus is administered by, for example, an injection into tissue 704 of a subject at any desired location depending on the particular procedure and/or treatment being conducted. In this particular embodiment, the syringe includes a detector 706 capable of sensing a radiation signal emitted from the bolus of labeled compound. The syringe also includes a power source 708, such as a battery, in electrical communication with the detector. In some embodiments, the detector may also be in electrical communication with a transmitter 710 that may wirelessly communicate a detected signal to a master controller of the medical detecting system, and/or any other appropriate computing device, prior to, during, and/or subsequent to administration. While a wireless transmitter has been depicted, it should be understood that as previously described, memory and/or wired connections may also be used for outputting the information as the disclosure is not so limited.

Figure 17:
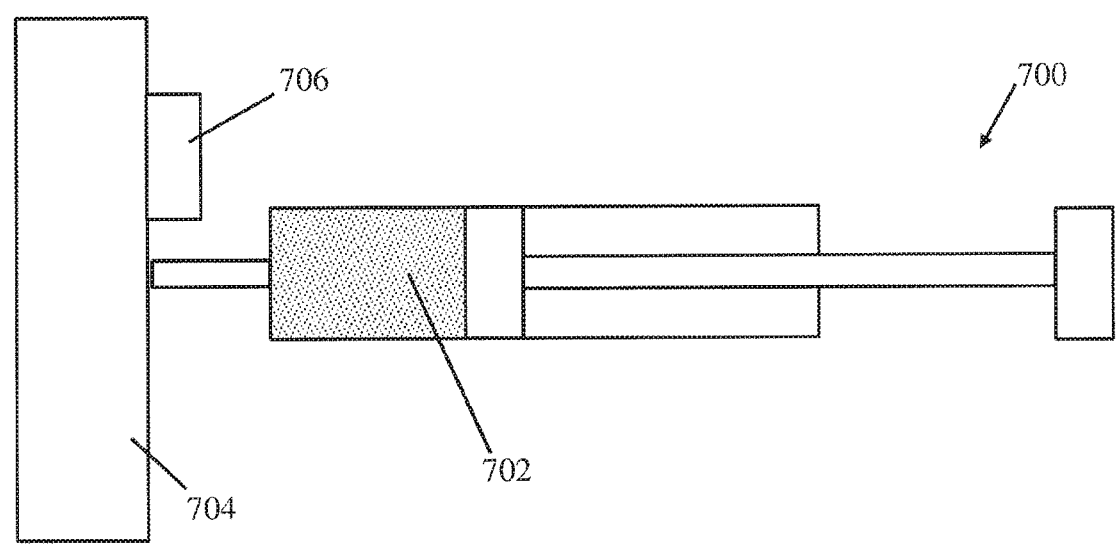
FIG. 17 is a schematic representation of a medical detecting system including a radiation detector at an administration site for a labeled compound labeled with a radioactive tracer.

FIG. 17 depicts another possible embodiment of a device for sensing an initial radiation signal from a bolus of labeled compound. In the depicted embodiment, a syringe 700 may be used to administer a bolus of labeled compound including a radioactive tracer into the tissue 704 of a subject. In this particular embodiment, a medical detecting system may include one or more detectors 706 located proximate to an administration site of the bolus into the subject's tissue. The depicted one or more detectors may be integrated into a wearable structure as previously described to both position and maintain the one or more detectors proximate to the desired administration site. Depending on whether or not shielding is used on the detector, a radiation signal emitted by the bolus of labeled compound may be sensed prior to, during, and/or after administration of the bolus into the subject's tissue. Again, this detected signal may be transmitted to a controller of the medical detecting system and/or an associated computing device in any appropriate manner including, but not limited to, wireless transmission, memory for subsequent download, and/or a wired connection as the disclosure is not so limited.

While a separate detector has been described above for detecting an initial signal associated with the administration of a labeled compound, in some embodiments, a system may simply include a user input such a button, an icon on a touch screen, or other appropriate type of input for indicating when a labeled compound has been administered and/or when other events have occurred. For example, this input may then be used by an associated controller to either activate a detecting system and/or tag an initial administration time of the labeled compound for subsequent signal analysis portions such as an initial detection and rise in a detected radiation signal.

While the one or more detectors of a medical detecting system may be used to simply determine threshold radiation signals for a particular application, in some embodiments, it may be desirable to measure dynamic radiation signals emitted from a particular body portion. This may permit the pharmacokinetic behavior of a particular labeled compound within a body portion of interest to be determined. The detected pharmacokinetic behavior of the labeled compound within the subject may then be compared to known pharmacokinetic behaviors of the labeled compound associated with particular disease states and/or treatment states. As described further below, a disease state and/or treatment state may be determined using any number of parameters associated with a particular detected signal including, but not limited to, a sensed signal ratio, a slope of the detected signal at one or more time points, an area under the curve over one or time intervals (i.e. the number of counts or intensity over a predetermined time interval), threshold signals, fit parameters, time constants, and/or any other appropriate pharmacokinetic parameter. Using the determined disease state and/or treatment state, a controller of the medical detecting system, and/or an associated computing device, may output a diagnosis, recommended treatment regimen, and/or control the operation of an associated treatment device depending on the particular embodiment.

Figure 18:
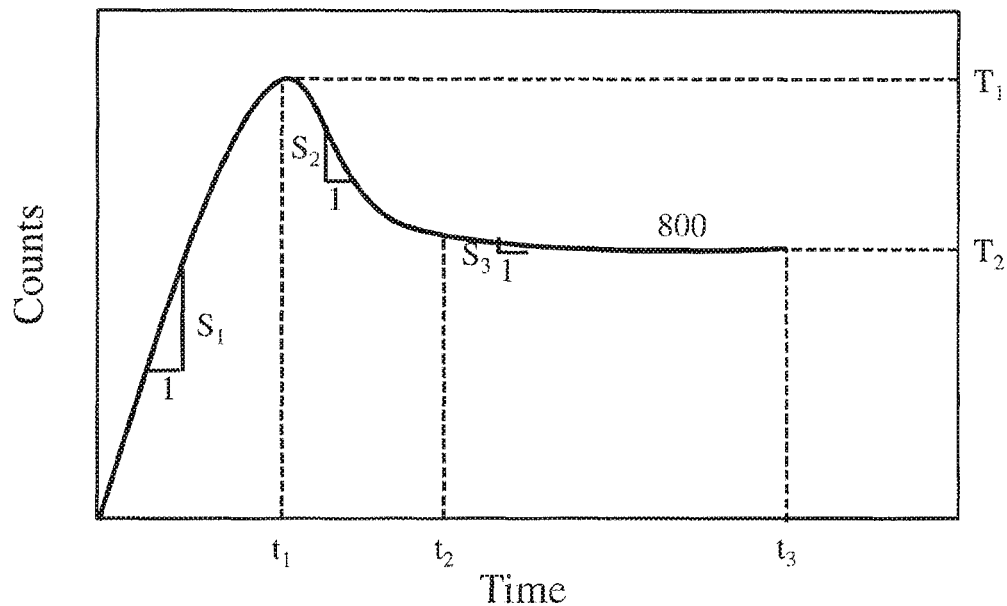
FIG. 18 is a schematic representation of a radiation signal emitted from a body portion that varies versus time.

FIG. 18 shows one exemplary curve of a radiation signal that may be measured by a detector for a labeled compound that reaches approximately a steady state concentration within a particular body portion during a predetermined time period. As seen in the figure, the detected signal initially rises with a positive slope $s_1$ to a peak located at threshold $T_1$ at time $t_1$ during a first time period. Without wishing to be bound by theory, this peak is due to non-specific binding of the labeled compound within the blood and/or other portions of the subject that subsequently clears from the body portion of interest over time. Consequently after reaching this initial peak, the signal declines during the second time period after $t_1$. The profile may exhibit a range of decreasing slopes during this transition period as indicated by a negative slope $s_2$. The detected signal may continue to decrease to a plateau or trough with a second smaller threshold $T_2$ as compared to the peak by a time $t_2$. Without wishing to be bound by theory, this second threshold may correspond to a detected signal associated with specific binding of the labeled compound within the body portion of interest. Within the body portion, this third time period of the detected signal may still have a smaller third slope $s_3$ that may either decrease and/or increase over time depending on the particular targeting moiety that has been used with the labeled compound. Monitoring of the detected radiation signal may continue until a predetermined time $t_3$. It should be noted, that the particular signal detected may vary based on whether a subject is in a resting or active state. Accordingly, depending on how a particular test and/or treatment is applied, the detected signal may be compared to a corresponding baseline established either for the individual subject, or a general population, in the same activity state.

Figure 19:
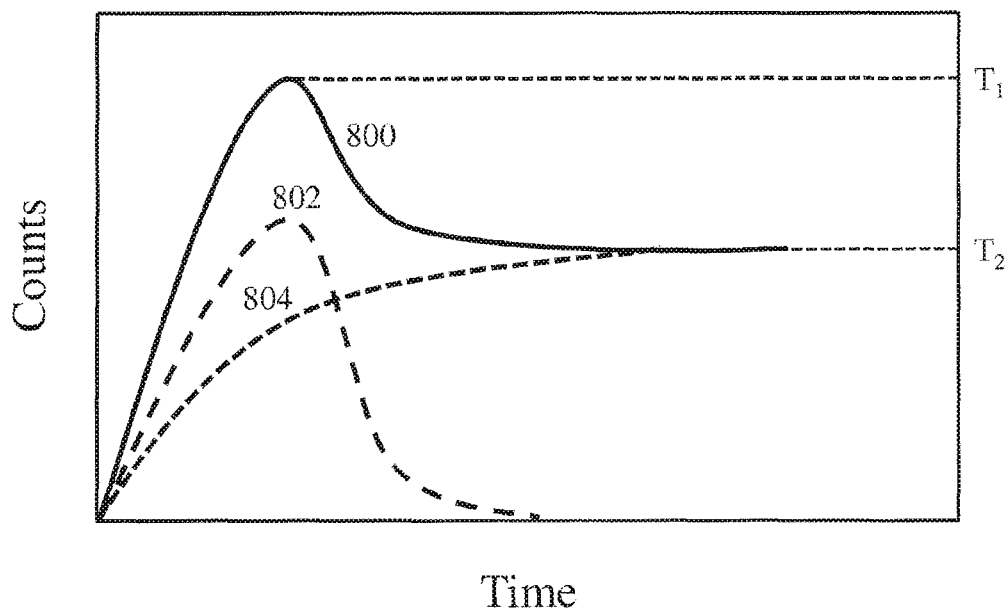
FIG. 19 is a schematic representation of a radiation signal emitted from a body portion that varies versus time with the separate contributions from both specific and non-specific radiation signals shown separately.

To help illustrate what is occurring in the above described exemplary radiation signal, FIG. 19 shows the same total signal 800 depicted in FIG. 18. However, the figure also includes the deconvolved signals corresponding to detected radiation signals associated with non-specific binding of the labeled compound 802 and the specific binding of the labeled compound 804 within the body portion. As illustrated in the figure, the non-specific signal increases more quickly than the specific signal prior to decreasing resulting in the observed peak. During this transitional period of the non-specific signal, the specific signal continues increasing to the steady state value observed at the plateau located after the non-specific peak. Leading to the eventual plateau signal that is observed during a later portion of the signal profile.

Figure 20:
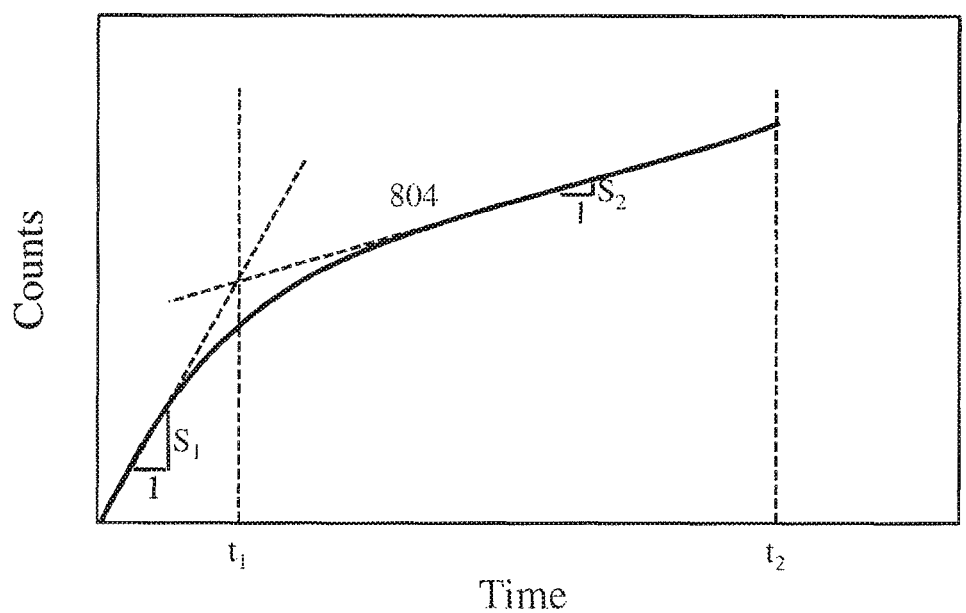
FIG. 20 is a schematic representation of a radiation signal emitted from a body portion that varies versus time.

FIG. 20 illustrates another exemplary curve of a radiation signal 804 that may be measured by a detector for a labeled compound that continually increases in concentration within a particular body portion during a particular monitoring period. Without wishing to be bound by theory, such a signal may correspond to a labeled compound including a target moiety that tightly binds with a target and does not reach an equilibrium state, and instead continues to saturate all of the available binding sites. Typically such a targeted labeled compound is not appropriate for use when monitored by radiation detectors for detection of a disease and/or treatment state because the signal does not reach a steady-state value that may be easily compared to a threshold value. However, using the pharmacokinetic behavior of the compound as measured using the systems and/or methods disclosed herein, and/or with any other appropriate medical detecting system, such a labeled compound may be used for medical diagnostic and/or treatment purposes. For example, the depicted radiation signal may increase throughout the duration of the monitored time period. However, the signal may exhibit different slopes such as a positive slope $s_1$ during a first time period up to time $t_1$ and a different positive slope $s_2$ during a second time period monitored up to time to $t_2$. In addition to the slopes, the radiation signal may exhibit one or more inflection points, see the inflection point at time $t_1$, an area under the curve during certain time periods, different time constants, or any number of other dynamic characteristics that may be used for comparative purposes to determine a particular disease or treatment state of a subject.

It should be understood that while several particular curves for a detected radiation signal have been discussed above and illustrated in the figures, any number of different types of curves and/or behaviors may be observed. For example different signals may be observed due to the use of different types of labeled compounds, different types of targeting moieties, different compound weights that affect the kinetics of the compounds, differences in how these compounds interact with different portions of a subject's body, and/or any other appropriate consideration that may affect the pharmacokinetic properties of a labeled compound. Additionally, an observed signal may be different from those described above due to the total observed signal including signals from different portions of the body including, for instance, the liver, skin, and/or other body portions in addition to the desired signal from the body portion of interest. However, regardless of the specific signal detected for a given body portion and labeled compound, using the various characteristics of the pharmacokinetic response it may be possible to compare those characteristics to corresponding characteristics previously measured and associated with known disease states and/or treatment states to determine a current disease state and/or treatment state of a subject.

The above embodiments have primarily been directed to detecting signals from a single labeled compound that has been administered to a subject. However, the currently disclosed systems, detectors, and methods are not limited to uses with a single labeled compound. For example, in some embodiments, a medical practitioner may administer a plurality of labeled compounds to a subject at once. For example, two or more different types of labeled compounds that emit different radiation signals with different energy levels may be administered to the subject. The labeled compounds may either include the same, and/or different, targeting moieties as the disclosure is not so limited. A corresponding medical detecting system used to detect radiation signals emitted by the different labeled compounds may include: one or more detectors that are sensitive to, and in some instances may be capable of discriminating between, radiation signals with at least two different energy levels; a first set of detectors that are sensitive to a radiation signal with a first energy level and at least a second set of detectors that are sensitive to a radiation signal with a second energy level different from the first; and/or a combination of these types of detectors. Similar to the other embodiments described above, the plurality of detected radiation signals emitted by the plurality of labeled compounds may be compared to one or more characteristics to determine either a treatment and/or disease state of a subject. One possible example of labeled compounds that may be administered to a subject at the same time include, but are not limited to, an 18F tau agent (e.g. AV-1451, THK5351, GTP-1, or MK6240) administered simultaneously with an $^{123}$I amyloid agent (e.g. $^{123}$I-ABC577).

In view of the above, in some embodiments, a labeled compound that exhibits non-specific binding may be administered along with a labeled compound that exhibits specific binding associated with a particular disease and/or treatment state. The resulting detected radiation signals associated with the separate specific and non-specific binding of the labeled compounds may then be compared with one another to determine a difference, ratio, or other appropriate comparison between the two signals. In some instances, the labeled compound exhibiting non-specific binding with a target portion of the body may be saturated in the target body portion prior to administering the labeled compound that exhibits specific binding. Additionally, to help with differentiating the signals, the labeled compounds may emit radiation with different energy levels.

Figure 21:
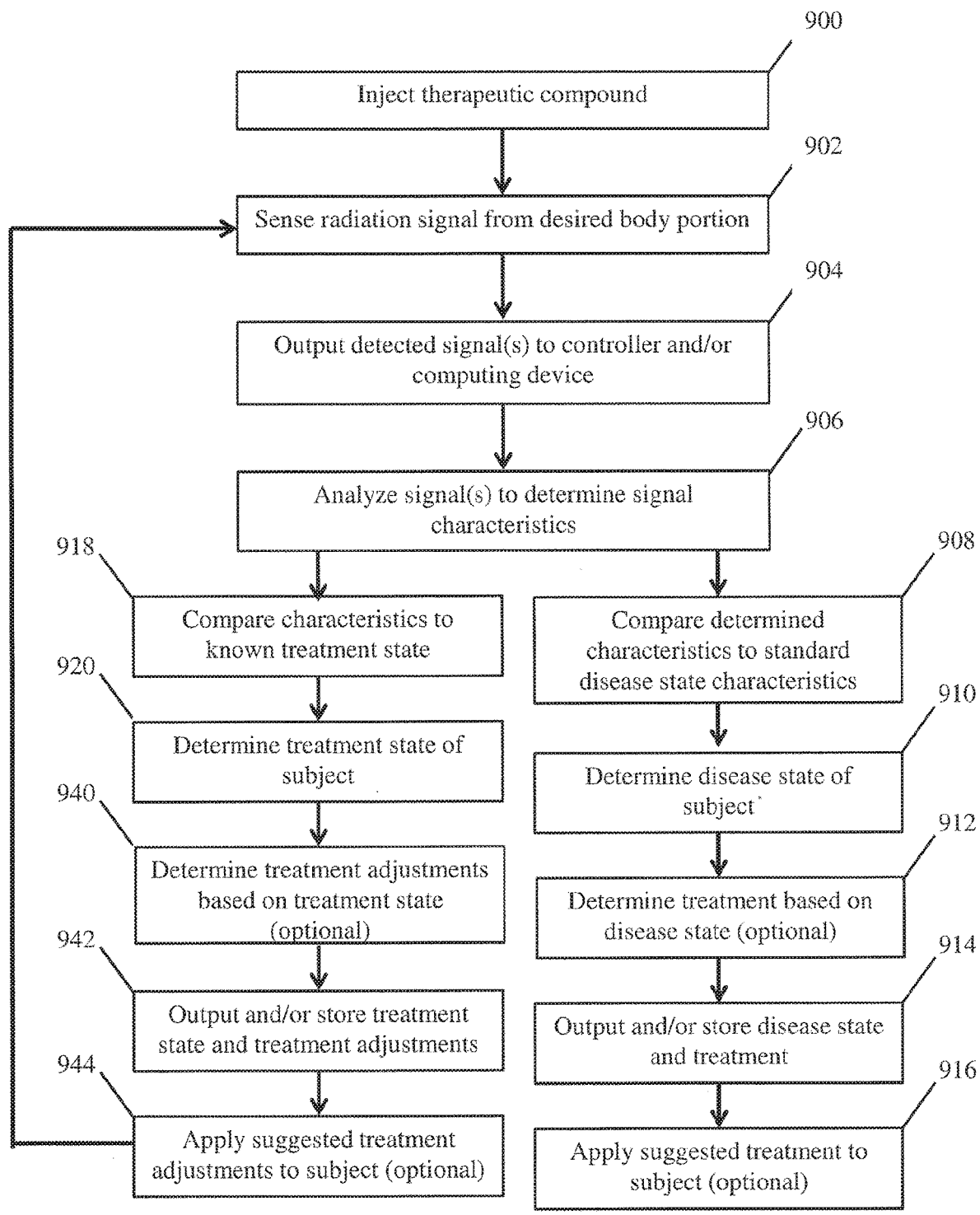
FIG. 21 is a flow diagram of a diagnostic and/or treatment method using the medical detecting systems described herein.

FIG. 21 illustrates one possible embodiment of a method where a medical detecting system is used to monitor a signal associated with a labeled compound administered to a subject for the purposes of medical diagnosis and/or treatment. In the figure, a labeled compound is administered to a subject by, for example, injection into tissue at a desired location of a subject at 900. As the labeled compound is distributed throughout one or more portions of the subject's body, one or more detectors of a medical detecting system may be used to sense one or more radiation signals emitted from a desired body portion at 902. It should be understood that any appropriate medical detecting system, including those described herein, may be used to monitor the desired signals.

Once the one or more signals are detected, the detectors may output the one or more signals to an associated one or more controllers, and/or any other appropriate computing device at 904. For example, using the above described embodiments, the signals may be received by a master controller that subsequently transmits the detected signals to an associated computing device such as a tablet or smart phone. The computing device may then analyze the one or more detected signals to identify one or more signal characteristics at 906. For example, in some embodiments, an algorithm executed on the computing device may determine the initial administration time of a labeled compound from the first detected rise in sensed activity of a signal from at least one detector. The computing device may then use a known dosage of the labeled compound, as may be measured with a detector at the location of administration and/or by one or more detectors associated with a device used to deliver the compound, to determine a normalized distribution of activity among the one or more detectors. Alternatively, a normalized signal may be generated by determining the ratio between a radiation signal detected at a portion of the body remotely located from the body portion of interest. For example, a detector placed on a torso, ankle, or wrist of a subject may be compared to the signals detected from a head of the subject.

Using either a raw and/or normalized signal, the one or more detected signals from the one or more detectors may then be analyzed to determine one or more characteristics illustrative of the pharmacokinetic properties of the labeled compound. These parameters include, but are not limited to, an area under the curve during one or more time periods, time constants, best fit exponential functions, time rate constants of the detected signals at one or more locations, differential equation models of the signals, peak detections, peak to trough or plateau ratios, volume of labeled compound distribution as measured with the medical detecting system, radiation field modelling and/or any other appropriate metric as the disclosure is not so limited. In some embodiments, the algorithm may also use spectral analysis to characterize variations in the signals associated with periodic events, such as a pulse and breathing of a subject.

A computing device may have standard characteristics, a range of characteristics, and/or a function that characterizes the determined characteristics of a radiation signal relative to a known disease state and/or a known degree of a particular disease state stored in an associated memory. Additionally, in some embodiments, these standards may take into account subject specific parameters such as body weight, height, race, dexterity, skull/hair circumference, detector location, and/or other appropriate subject characteristics to determine a particular characteristic or range of characteristics associated with a disease state for the subject being tested. For example, a taller or heavier individual may exhibit an increased time, and corresponding time constants, for a labeled compound to reach its equilibrium state than a lighter shorter individual. In either case, using whichever standard and characteristic is appropriate for a given application, a computing device may compare the determined signal characteristics of a detected signal from the one or more detectors to the standard characteristics stored in the computing devices memory to identify a current disease state of the subject at 908 and 910. For example, in one specific embodiment, a computing device may have an estimator that compares radiation field measurements at one or more position within a body portion of interest over a predetermined time period to one or more standard characteristics, to calculate a diagnosis D. In general, a diagnosis D may be a linear, or nonlinear, fit of one or more characteristics of the radiation signals measured for a known disease state as determined using a group of subjects with the known disease states and/or burdens/severities of that disease state under known and/or measured radiation fields after the administration of a given labeled compound. Further, this comparison and/or function may be used to determine if there is no detected disease, a detected disease, and/or a particular severity of the disease state by determining the disease state and/or severity of a disease state that best matches the detected signal as measured by the detectors. In addition to determining the effectiveness of a particular treatment, and/or to diagnose a particular condition, the disclosed systems and methods may also be applied to help develop agents that target particular anatomical structures. For instance, a medical detecting system may be used to quickly and cheaply evaluate the affinity particular agents have for different anatomical structures. This may be of benefit when developing compounds to target specific portions of a subject's body for treatment and/or diagnostic purposes.

In one specific example, a system may estimate amyloid burden within a subject's brain after the administration of an isotope that binds to beta-amyloid plaques (e.g. florbetapir, flutemetamol, florbetaben, NAV4694, C11-PIB, 18F-FACT, 123I-ABC577, an antibody or an antigen-binding fragment thereof etc.). In such an embodiment, data from a set of individuals with varying and known degrees of amyloid burden (that has already characterized by their relative concentration of a given ligand in the grey matter versus the cerebellum) may be measured with known radiation fields as measured with radiometers and/or derived from 3D nuclear images. The various input parameters may then be analyzed to determine one or more signal characteristics that best correlate with amyloid burden to determine a function of those characteristics versus measured signal characteristics. This function, and/or range of characteristics of the radiation signal at one or more points within the subject's brain may be used to estimate a degree of amyloid burden in other subjects where the radiation signal emitted from those same locations are measured. Of course it should be understood that while a particular disease state related to a degree of amyloid burden has been described above, the concepts of using a known ranges of characteristics correlated with, and/or a function fit to, a known disease state may be used for determining any appropriate type of condition as previously discussed.

Once a disease state of a subject has been determined, in some embodiments, a computing device may also include a number of different treatments that are appropriate for treating the detected disease state stored in memory. Based on the type of disease state and/or a severity of the identified disease state, the computing device may optionally determine an appropriate treatment for the subject at 912. For example, in a particular embodiment, treatment and further PET imaging may be recommended for subjects that have high estimation of amyloid burden. Further, the computing device may recommend amyloid reducing agents, such as an anti-ab antibody or antigen-binding portion thereof (e.g., aducanumab or solanezumab) for those subjects estimated to have a level of amyloid burden above a given threshold. Further, doses of particular labeled compounds may be determined and output to a user based on the determined disease state and appropriate subject considerations, e.g. the estimation of amyloid burden, and treatment of the condition, could be monitored with the systems described herein as discussed below. In one embodiment, it may be desirable to use different compounds for detection and therapy.

While, the computing device may determine possible treatment options in the embodiment above, embodiments in which the computing device does not determine treatment options are also contemplated as the disclosure is not so limited.

After determining a disease state of a subject, and optionally determining treatment options for the disease state, the computing device may output the determined disease state and/or treatment options at 914 to a display, print out, other computing device, and/or any other appropriate medium. The medical practitioner viewing the output disease state and/or treatment may then apply the suggested treatment to the subject and/or may order additional testing of the subject to confirm the indicated disease state and/or treatment options. Alternatively, the disease state and/or treatment options may be: stored in memory; transmitted to a remotely located computing device, cloud server, or other database; and/or otherwise stored for subsequent readout, access, processing, manipulation, and/or subsequent transmission as the disclosure is not limited in this fashion.

In instances where data is transmitted to a remotely located computing device, cloud server, or other database, the transmitted data may be included in a dataset including data from a plurality of other subjects. Thus, a pool of data including characteristics associated with signals detected for a number of different subjects may be compiled in a single dataset. Further, the newly transmitted data may be used to both, grow, update, and establish a more representative pool of signal characteristics used to identify a particular disease state. For example, an average signal characteristic, as well as standard deviations within a population, corresponding to any of the characteristics noted above may be updated for each signal associated with the presence, and/or absence, of a particular disease state input into the database. Additionally, the data may be subdivided by age, gender, height, weight, ethnicity, and/or any other appropriate physical characteristic. These subdivided datasets may be analyzed to determine averages and/or standard deviations for signal characteristics used to identify the presence and/or absence of particular disease states using these physical characteristics as variables for a given population. Thus, in view of the above, a growing population set for use in determining appropriate standard characteristics for analyzing detected signals may be implemented in some applications.

In addition to determining a particular disease state, the described medical detecting systems may also be used to monitor the treatment of a subject and/or to actively control the operation of a treatment device used to apply a treatment to a subject. Similar to the above embodiment, a labeled compound may be administered to a subject at 900. The resulting radiation signals from a desired body portion may be monitored using one or more detectors prior to being output to a controller and/or computing device where it is analyzed to determine one or more signal characteristics at 902-906 as previously described. These determined signal characteristics may then be compared to a standard range of characteristics and or a standard function related to the detected characteristics at 918 determined from known treatment states to determine a current treatment state of the subject at 920. For example, the signal characteristics may indicate whether an effective amount, for either therapeutic, diagnostic, and/or baseline purposes, of a labeled compound, such as a beta-amyloid blocker, anesthetic, cancer drug, or other labeled compound is reaching the body portion of interest in the correct concentration, too little a concentration, too great a concentration, for too short a duration, and/or for too long a duration. Of course, other treatment states such as the distribution of a labeled compound at different locations within one or more body portions as well as any other appropriate state may be monitored as well. Based on the above, at 940, the computing device may determine appropriate treatment adjustments based on the treatment state including, but not limited to: continuing treatment for a desired treatment duration after detecting an initial radiation signal; increasing a delivery rate of a labeled compound; decreasing a delivery rate and/or stopping delivery of a labeled compound; delivering an additional bolus of a labeled compound; apply one or more physical stimuli to a subject (e.g. physical manipulation or vibration of a body portion, electrical stimuli, heat, cold, exercise, etc.); and/or any other appropriate adjustments that may be made to a particular type of treatment. Alternatively, if the detected treatment state is the same as a desired treatment state of the subject, the computing device may determine that the current delivery parameters of a labeled compound should be maintained.

Similar to the above described embodiment, a determined treatment state and/or possible treatment adjustments for a particular subject may be output and/or stored in memory for subsequent download, transmission, and/or other usage at 942 similar to that described above for the output of disease states and/or treatment options. For example, in instances where data is transmitted to a remotely located computing device, cloud server, or other database, the transmitted data may again be included in a dataset including data from a plurality of other subjects. Additionally, this dataset may be analyzed and updated as previously described to determine appropriate averages and/or standard deviations for one or more signal characteristics associated with one or more populations in the dataset.

While a practitioner may review the determined treatment state of a subject and possibly implement the suggested treatment adjustments, in at least one embodiment, the determined treatment adjustments may be transmitted from the computing device to a treatment device in either electrical or wireless communication with the computing device to automatically adjust operation of the treatment device. As indicated in the figure, this adjustment in operation may be implemented either discretely or in a feedback loop. Thus, after adjusting the treatment of a subject, the system may continue to sense the emitted radiation signals from the body portion of interest while determining the treatment state of the subject for possible future adjustments of the applied treatment. This feedback loop may be continued until an effective amount of labeled compound has been supplied to the body portion of interest, until a desired duration of treatment has expired, a procedure on the subject has been completed, and/or any other appropriate event has occurred as the disclosure is not so limited. Additionally, the feedback loop may either be done continuously and/or at predetermined intervals to permit sufficient time for the treatment adjustments to create changes in the detected radiation signal.

Figure 22:
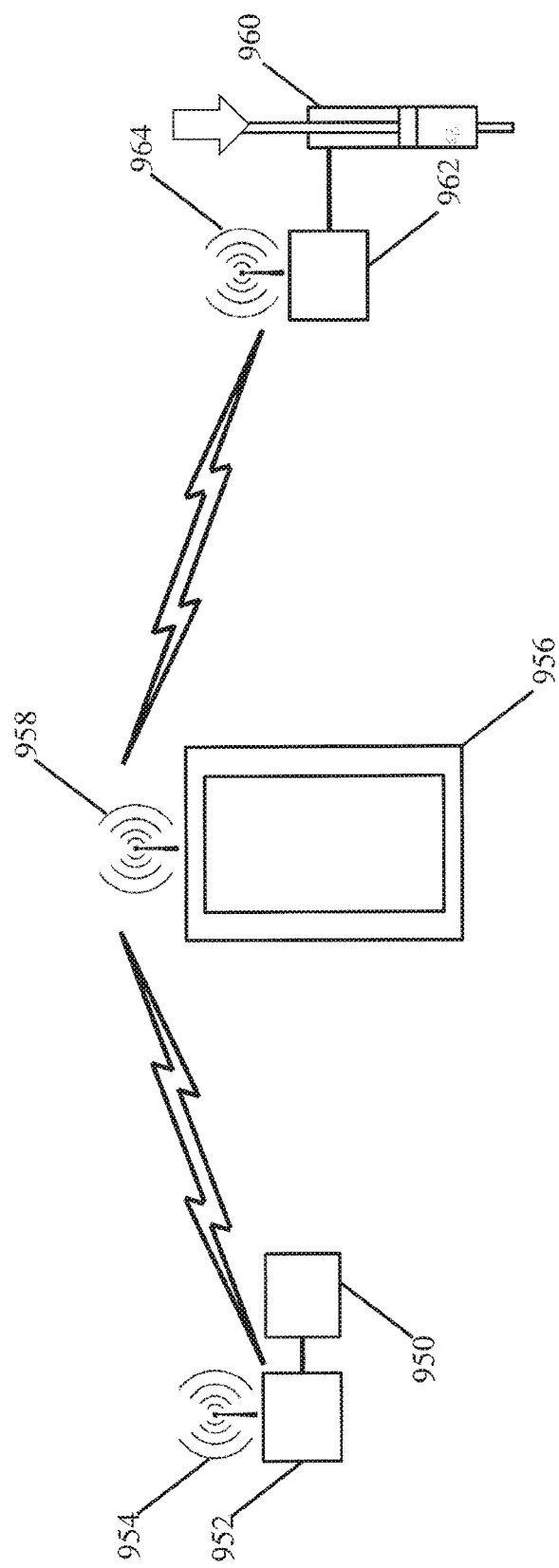
FIG. 22 is a schematic representation of a treatment device controlled using a medical detecting system.

One embodiment of a medical detecting system being used to control the operation of a treatment device is shown in FIG. 22. In the depicted embodiment, one or more detectors 950 detect a radiation signal emitted from an associated body portion, not depicted. This detected signal is transmitted to a controller 902 in electrical communication with the one or more detectors. The controller then transmits the detected signals via a transmitter 954 to a transmitter 958 in electrical communication with a computing device 956. The computing device may determine the treatment state of the subject, and one or more desired adjustments to the currently applied treatment, as previously described. The computing device may then send one or more commands and/or signals to a controller 962 of the detecting system that is then transmitted via transmitter 964. The controller 962 may be in electrical communication with the desired treatment device 960. Consequently, the controller may command the treatment device to alter one or more operating parameters of the treatment device to provide the desired treatment adjustments communicated from the computing device. For example, in some embodiments, the labeled compound being monitored may delivered by a treatment device such as a needle or catheter associated with a pressure generating device such as a peristaltic pump, displaceable syringe, or other device. In such an embodiment, an operating speed and/or duration of operation of the pump may be altered to either initiate, increase, decrease, change the delivery profile of and/or stop the rate delivery of the labeled compound to the subject. Therefore, it should be understood that any appropriate operating parameter may be adjusted including, but not limited to, pressure, delivery rate, duration of treatment, volume delivered, and/or any other appropriate operating parameter. Additionally, other types of treatment devices that do not directly administer the labeled compound to a subject may also be controlled. For instance, vibrational devices, electrodes, heaters, coolers, and/or any other appropriate type of treatment device may be controlled.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computing device or distributed among multiple computing devices. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computing device may be embodied in any of a number of forms, such as one or more integrated processors, a rack-mounted computer, a desktop computer, a laptop computer, or a tablet computer. Additionally, a computing device may be embedded in a device not generally regarded as a computing device but with suitable processing capabilities, including a Personal Digital Assistant (PDA), a smart phone, a tablet, or any other suitable portable or fixed electronic device. Further, while a separate computing device may be used, in some embodiments, a computing device, such as one or more processors and associated memory, may be integrated with a medical imaging system; a treatment device such as a syringe and/or pump; or any other appropriate component or system described herein as the disclosure is not so limited.

Also, a computing device may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Such computing devices may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the disclosed embodiments may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a non-transitory computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program", "algorithm", or "software" are used herein in a generic sense to refer to any type of computer code or set of computer-executable instructions that can be employed to program a computing device or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

EXAMPLE

Methods

Tests were conducted using a series of radiometers positioned around subjects heads and a standard PET camera using the amyloid tracer $^{18}$F-fluorbetapir in subjects with probable Alzheimer's disease (AD subjects) and healthy control volunteers (HC). $^{18}$F-fluorbetapir is a radioactive diagnostic agent for positron emission tomography (PET) imaging of the brain to estimate β-amyloid neuritic plaque density in adult patients with cognitive impairment who are being evaluated for AD. PET imaging targeting β-amyloid neuritic plaque deposition has already begun playing a role in identifying individuals very early in the course of AD and monitoring progression of the disease over the course of the treatment with investigational therapeutics.

During testing, $^{18}$F-fluorbetpir was administered intravenously as a bolus injection followed by a saline flush. Prior to imaging, subjects had an IV catheter (for radiotracer infusion) inserted. Each subject received a single injection of the radioligand with a dose of no more than 10 mCi in a maximum volume of 10 mL.

The device included a cap fitted with up to 5 detectors at various 10-20 EEG positions which was placed on the subject's head. The subjects were asked to avoid any movements of the head and to remain immobilized as much as possible. Additional detectors were secured to one ankle and the chin to obtain an indirect measure of the activity in the blood, and to monitor activity in the head respectively. In one subject, an additional detector was mounted 8.5 cm above a detector located on the top of the subject's head. Detector specific count rates and total counts were measured continuously for up to 3 hours. The count rate and total counts were compared in the AD subjects and HC subjects to extrapolate qualitative and quantitative pattern differences. During testing, detectors were maintained at approximately 19 mm±4 mm from the skull, and were within 15 degrees of symmetric left right positioning as confirmed by CT measurements.

For processing purposes, detected radiation signals were decay corrected to the time of injection. The counts were recorded in 4 second intervals, which were then median filtered using a 2 minute window. Periods with high noise counts on a detector were excluded from analysis. PET scans were conducted concurrently on the subjects while data was collected with the radiation detectors to confirm the measurements and subject AD condition.

Alzheimer's Disease Detection

Figure 23:
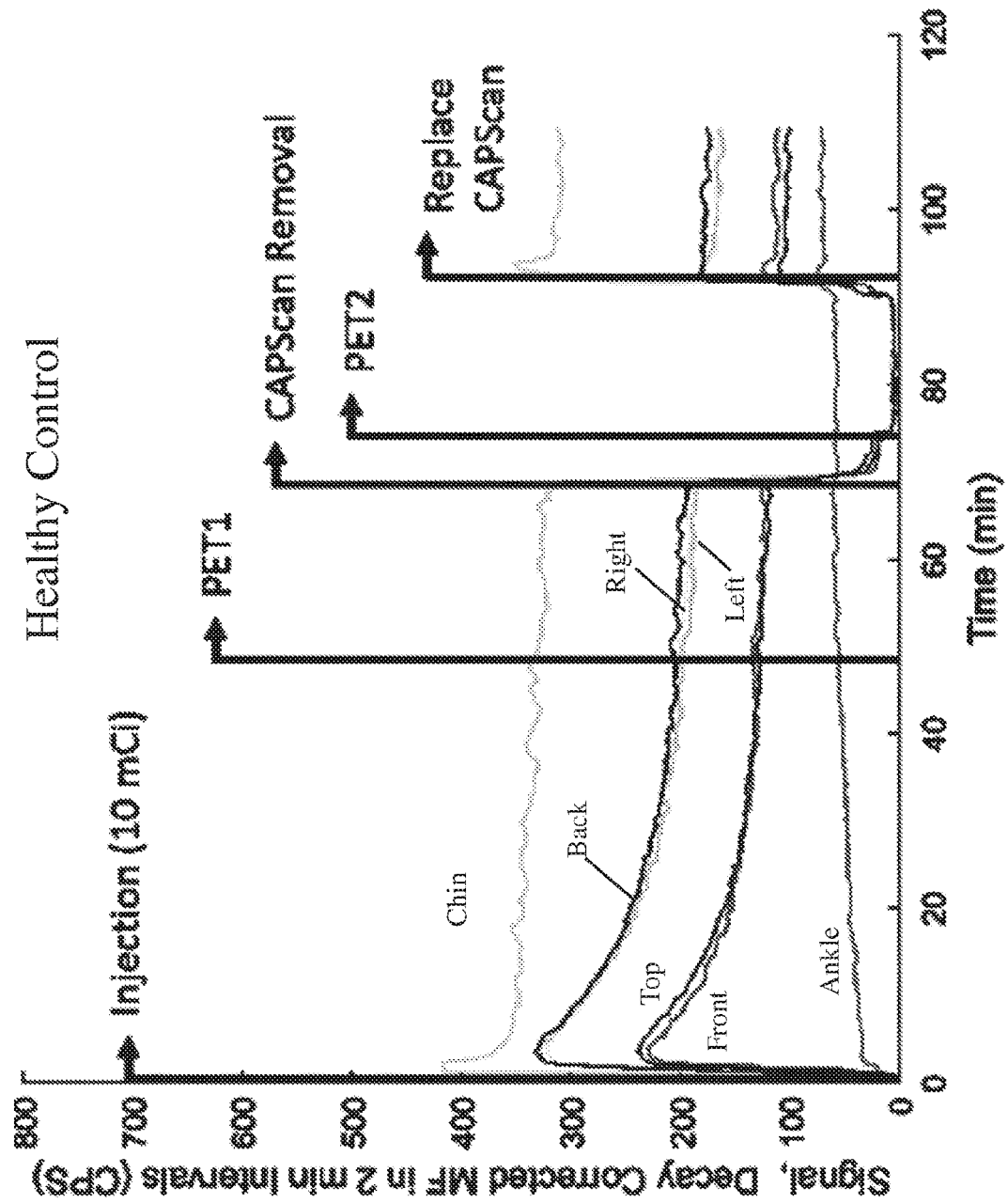
FIG. 23 is a graph of radiation signals detected with multiple detectors distributed around the head of a healthy subject after being administered a radioactive probe that targets amyloid beta.
Figure 24:
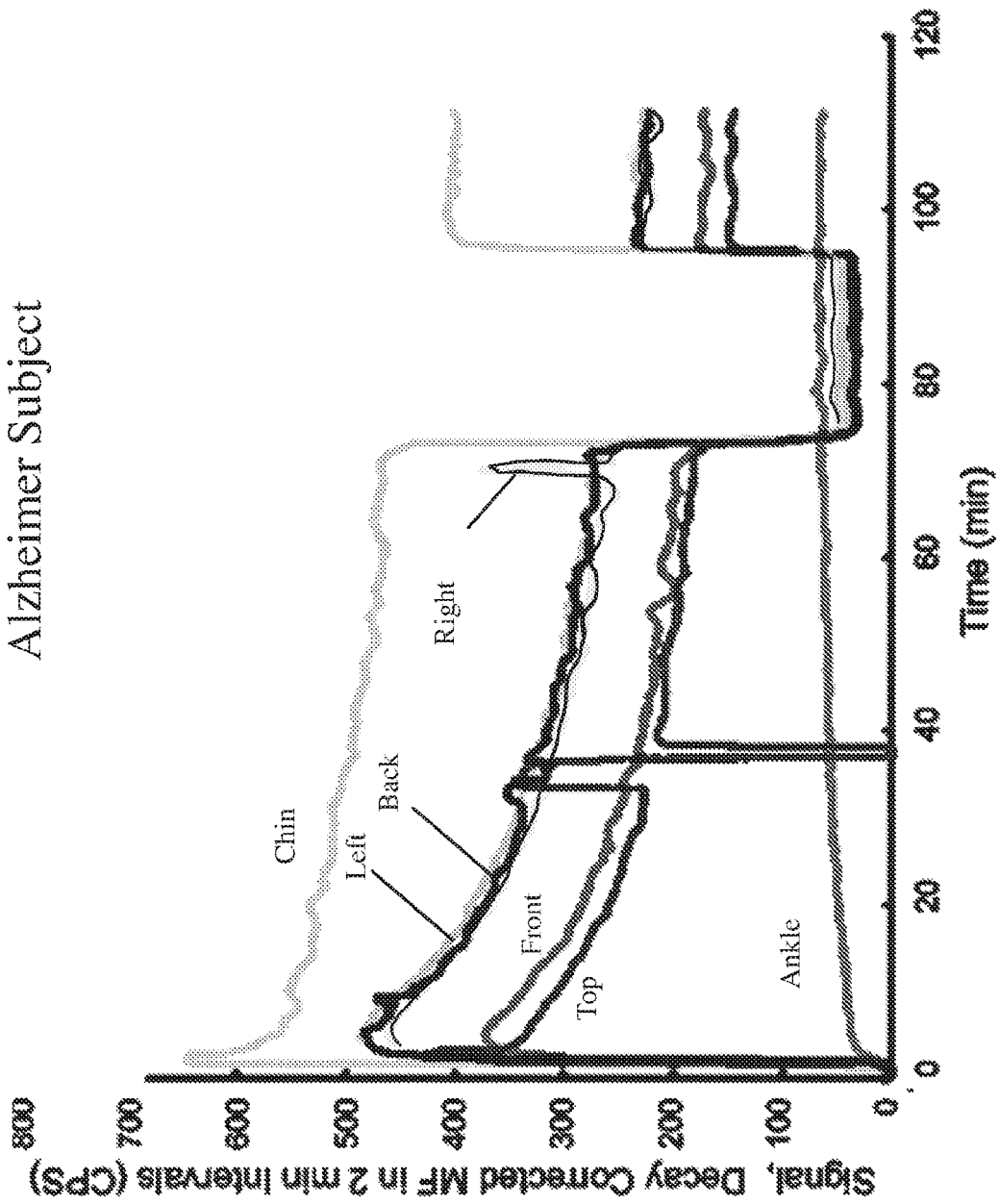
FIG. 24 is a graph of radiation signals detected with multiple detectors distributed around the head of a subject with probable Alzheimer's disease after being administered a radioactive probe that targets amyloid beta.

FIGS. 23 and 24 are representative graphs of radiation signals measured by detectors at different locations around the subjects head for a healthy and AD subject respectively. As shown in the figures, the signals for the healthy and AD subjects were similar. There were no large scale differences in the overall magnitude of the detected signals, or in the ratios of peak to trough. Additionally, it was observed that the ankle detector signals steadily climbed after injection in all subjects. Without wishing to be bound by theory, this suggests that the observed signals correspond to a labeled compound that does not readily unbind from tissue when the concentration in the blood drops.

Upon further analysis of the data, a faster initial washout was observed in the signals for healthy subjects. To quantify this, a constrained bi-exponential model was fit to the 10-65 minute period of each of the detectors, as well as the sum of the brain signals (excluding the chin, ankle and tip top detectors). The alpha phase was limited to a 5-30 min half-life, and the beta phase to 30 minutes or longer half-life.

$$S = Ae^{\alpha t} + Be^{\beta t}$$

In the above equation, S is the signal magnitude, A and B are fitting parameters, $\alpha$ and $\beta$ are time constants, and t is time. Using this equation, the four parameters of the bi-exponential were compared with the average cortical standardized update value ratio (SUVR). The fractional size of the alpha compartment (A/(A+B)), and a combination of this metric with a (which is proportional to the initial slope of the alpha compartment) were also compared with the average cortical SUVR. It was noted that healthy subjects exhibited a faster alpha phase than AD subjects. This correlation was evident in the aggregate brain signal (R($\alpha$,SUVR) Brain=0.96) and in most of the individual brain detectors (correlations 0.98, 0.97, 0.88 for the top, right, and front, and a lower 0.46 and 0.18 for the back and left). Without wishing to be bound by theory, this signal may be due to faster perfusion and reduced amyloid binding leading to faster clearance; confirming that it is possible to identify a disease state using the kinetics of the measured radiation signals.

In addition to the above noted difference in kinetics, it was noted that the detected radiation counts were proportional to total activity in the detector's field of view. This suggests that if a biomarker exists that is proportional to the total activity in the head associated with a particular disease state, the devices described herein can be used to measure this activity and differentiate between healthy and diseased states using a thresholding strategy. For example, for amyloid detection there are existing ligands, and ligands under development, that exhibit a more pronounced difference in overall uptake with amyloid burden (e.g. C11-PIB, NAV4694, 123I-ABC577, FAB2) than Florbetapir. Therefore, it is possible that radiation signals exhibiting different magnitudes, ratios, kinetics, and/or other parameters may also be observed when using more amyloid specific ligands.

Replacement Sensitivity

For four of the five subjects, cap replacement data was collected. For three of the subjects the detected radiation signals were relatively unchanged upon replacement of the cap as illustrated by the portions of the signals in FIGS. 23 and 24 corresponding to when the caps were removed and subsequently replaced. For one subject, the radiation signals did not clearly resume. It was confirmed that the signal that did not resume was likely due to difference in distance to the subject's skull due to their hair. Accordingly, the described devices may be used to measure reproducible radiation signals due to easy of placement and use. Additionally, difference in measured signals due to differences in placement may be minimized by moving the detectors further away from the skull to minimize the percent variability in distance between the skull and detectors and/or using a registration system to help position the detectors relative to a subject's skull.

Signal Ratios Associated with Different Positions

A forward model of a subject's head was used to estimate the radiation fields outside of the head from activity detected from within the head for each of the above noted subjects. The pattern of activity within the head was determined from a corresponding PET image. The forward model took into consideration the distance and attenuating tissue between each point within the head to each point beyond the head, within 5 cm of the skull. For each subject the radiation field created by labeled compound located within the brain was compared to the radiation field detected outside of the brain. The ratio of these fields (brain field/non brain field) yielded a signal to noise ratio (SNR) at each point beyond the head. It was identified that the region above the apex of the head had a higher SNR value (about 1.5) than other regions. Among several subjects the region was centered on the top rear of the head (PZ in EEG 10-20 positioning) and extended to regions include positions CZ, P3, O1, O2, and P4 in EEG 10-20 positioning. Among other subjects the region was shifted more forward; centered on CZ, and extending to FZ, C4, P4, PZ, P3, and C3 in EEG 10-20 positioning. This apical SNR stayed the same or increased with distance away from skull. In addition to the above, it was noted that two of the 5 subjects had high SNR value for detectors located at the side of their heads above the ears at locations F3, C3, P3, F4, C4, and P4. The increased SNR value decreased with increasing distance from the head.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A medical detecting system comprising:
a wearable structure for wearing on a body portion of a subject, wherein the body portion is a head of the subject;
one or more radiation detectors coupled to the wearable structure such that the one or more radiation detectors are positioned proximate to the body portion and distanced from a skin of the body portion of the subject when the wearable structure is worn by the subject, wherein the one or more radiation detectors are configured to detect radiation emitted from within the body portion; and
one or more spacers associated with the one or more radiation detectors and disposed between the one or more radiation detectors and the skin of the body portion when the wearable structure is worn by the subject, wherein the wearable structure is configured to bias the one or more radiation detectors and the one or more spacers against the body portions and wherein the one or more spacers are configured to apply a pressure to the skin of the body portion to reduce a flow of blood to the skin of the body portion when the wearable structure is worn by the subject.

2. The medical detecting system of claim 1, wherein the one or more radiation detectors are disposed within the wearable structure.

3. The medical detecting system of claim 1, wherein the one or more radiation detectors are maintained between 1 cm and 15 cm from a surface of the body portion.

4. The medical detecting system of claim 1, wherein at least one of the one or more radiation detectors are located on a top of the subject's head when the wearable structure is worn by the subject.

5. The medical detecting system of claim 4, wherein the one or more radiation detectors are centered at Cz or Pz in a 10-20 electroencephalogram (EEG) layout.

6. The medical detecting system of claim 1, wherein at least one of the one or more radiation detectors are located above the subject's ears and between a temple and a rear of the subject's head when the wearable structure is worn by the subject.

7. The medical detecting system of claim 6, wherein the one or more radiation detectors are disposed on a portion of the wearable structure corresponding to a region including F3, C3, and P3 and/or F4, C4, and P4 in a 10-20 electroencephalogram (EEG) layout.

8. The medical detecting system of claim 1, wherein the one or more radiation detectors are sensitive to radiation signals with at least two different energy levels.

9. The medical detecting system of claim 1, wherein the wearable structure is made of a compressive material and the compressive material is at least one of a flexible fabric, web, or non-woven material.

10. The medical detecting system of claim 1, wherein the one or more radiation detectors are configured to be re-arranged to accommodate a different body portion.

11. The medical detecting system of claim 1, wherein the one or more radiation detectors are configured to detect radiation emitted from the body portion through a portion of the skin with reduced blood flow.

12. A method comprising:
  positioning a wearable structure on a body portion of a subject, wherein the body portion is a head of the subject, wherein positioning the wearable structure also positions and biases one or more radiation detectors and one or more spacers associated with the one or more radiation detectors against the body portion, wherein the one or more spacers are disposed between the one or more radiation detectors and a skin of the body portion of the subject;
  maintaining a distance between the one or more radiation detectors and a surface of the body portion of the subject;
  detecting radiation emitted from within the body portion using the one or more radiation detectors; and
  applying a pressure to the skin of the body portion with the one or more spacers to reduce a flow of blood to the skin of the body portion.

13. The method of claim 12, further comprising positioning at least a portion of the wearable structure between the one or more radiation detectors and the surface of the body portion to maintain the distance between the one or more radiation detectors and the surface of the body portion.

14. The method of claim 12, wherein the one or more radiation detectors are maintained between 1 cm and 15 cm from the surface of the body portion.

15. The method of claim 12, further comprising positioning at least one of the one or more radiation detectors on a top of the subject's head when the wearable structure is worn by the subject.

16. The method of claim 12, further comprising positioning at least one of the one or more radiation detectors above the subject's ears and between a temple and a rear of the subject's head when the wearable structure is worn by the subject.

17. The method of claim 12, wherein detecting radiation further comprises detecting at least two radiation signals with different energy levels emitted from within the body portion using the one or more radiation detectors.

18. The method of claim 12, wherein the wearable structure is made of a compressive material and the compressive material is at least one of a flexible fabric, web, or non-woven material.

19. The method of claim 12, further comprising re-arranging the one or more radiation detectors to accommodate a different body portion.

20. The method of claim 12, wherein reducing the flow of blood to the skin reduces a skin signal sensed by the one or more radiation detectors.

\* \* \* \* \*